United States Patent
Fadell et al.

(10) Patent No.: US 10,262,508 B2
(45) Date of Patent: *Apr. 16, 2019

(54) SMART DEVICE WITH INTEGRATED CONDITIONAL LIGHTING

(71) Applicant: Google LLC, Mountain View, CA (US)

(72) Inventors: Anthony M. Fadell, Portola Valley, CA (US); Nick Webb, Menlo Park, CA (US); Matthew L. Rogers, Los Gatos, CA (US); David Sloo, Menlo Park, CA (US); Yoky Matsuoka, Palo Alto, CA (US); Adam Mittleman, Redwood City, CA (US); Shigefumi Honjo, Santa Cruz, CA (US)

(73) Assignee: Google LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/845,019

(22) Filed: Dec. 18, 2017

(65) Prior Publication Data
US 2018/0110106 A1    Apr. 19, 2018

Related U.S. Application Data

(63) Continuation of application No. 15/448,733, filed on Mar. 3, 2017, now Pat. No. 9,900,958, which is a
(Continued)

(51) Int. Cl.
G08B 5/36       (2006.01)
G08B 17/10      (2006.01)
(Continued)

(52) U.S. Cl.
CPC ............... *G08B 5/36* (2013.01); *F24F 11/30* (2018.01); *F24F 11/33* (2018.01); *F24F 11/34* (2018.01);
(Continued)

(58) Field of Classification Search
CPC ...... G08B 29/02; G08B 29/04; G08B 25/008; G08B 25/08; G08B 21/14; G08B 21/18;
(Continued)

(56) References Cited

U.S. PATENT DOCUMENTS 7,649,472 B1 *  1/2010  Paterno ............... F21V 33/0076
                                                     307/116
8,172,154 B1    5/2012  Figley et al.
(Continued)

OTHER PUBLICATIONS

Non-Final Office Action dated Jun. 13, 2016, for U.S. Appl. No. 14/508,182, 40 pages.

*Primary Examiner* — Mirza F Alam
(74) *Attorney, Agent, or Firm* — Kilpatrick Townsend & Stockton LLP

(57) ABSTRACT

Various arrangements of smart devices and systems are presented. Such smart devices and systems may include a wireless interface, a light sensor that detects an ambient brightness level of an ambient environment of the smart device, a motion sensor that detects motion of a user in the ambient environment of the smart device, a light that is capable of outputting light into the ambient environment of the smart device, and a processing system. The processing system may cause the light to illuminate based on: the message indicating that the lighting feature has been activated; the ambient brightness level being below the threshold brightness value; and the user moving in the ambient environment of the smart device or system.

20 Claims, 13 Drawing Sheets

Related U.S. Application Data continuation of application No. 14/508,302, filed on Oct. 7, 2014, now Pat. No. 9,646,480.

(60) Provisional application No. 61/887,969, filed on Oct. 7, 2013, provisional application No. 61/887,963, filed on Oct. 7, 2013.

(51) Int. Cl.

| | | |
|---|---|---|
| *F24F 11/30* | (2018.01) | |
| *G01N 27/02* | (2006.01) | |
| *G01N 27/12* | (2006.01) | |
| *G01N 33/00* | (2006.01) | |
| *G08B 25/00* | (2006.01) | |
| *G08B 21/18* | (2006.01) | |
| *G08B 29/18* | (2006.01) | |
| *G08B 3/10* | (2006.01) | |
| *G08B 21/14* | (2006.01) | |
| *H04L 12/28* | (2006.01) | |
| *G08B 5/22* | (2006.01) | |
| *G08B 21/12* | (2006.01) | |
| *G08B 25/01* | (2006.01) | |
| *G08B 29/02* | (2006.01) | |
| *G08B 29/04* | (2006.01) | |
| *G08B 29/26* | (2006.01) | |
| *G08B 17/117* | (2006.01) | |
| *G08B 29/22* | (2006.01) | |
| *H04L 29/08* | (2006.01) | |
| *F24F 11/33* | (2018.01) | |
| *G01J 1/42* | (2006.01) | |
| *G01V 8/10* | (2006.01) | |
| *H05B 33/08* | (2006.01) | |
| *H05B 37/02* | (2006.01) | |
| *G06T 7/70* | (2017.01) | |
| *G06K 9/00* | (2006.01) | |
| *H04M 1/725* | (2006.01) | |
| *H04N 7/18* | (2006.01) | |
| *F24F 11/34* | (2018.01) | |
| *G08B 25/08* | (2006.01) | |
| *F24F 120/10* | (2018.01) | |
| *F24F 11/46* | (2018.01) | |
| *F24F 11/58* | (2018.01) | |
| *G08B 19/00* | (2006.01) | |
| *F24F 11/75* | (2018.01) | |
| *F24F 11/89* | (2018.01) | |
| *F24F 11/70* | (2018.01) | |

(52) U.S. Cl.
CPC ............ *G01J 1/4204* (2013.01); *G01N 27/02* (2013.01); *G01N 27/121* (2013.01); *G01N 33/004* (2013.01); *G01N 33/0031* (2013.01); *G01V 8/10* (2013.01); *G06K 9/00744* (2013.01); *G06T 7/70* (2017.01); *G08B 3/10* (2013.01); *G08B 5/22* (2013.01); *G08B 17/10* (2013.01); *G08B 17/117* (2013.01); *G08B 21/12* (2013.01); *G08B 21/14* (2013.01); *G08B 21/18* (2013.01); *G08B 21/182* (2013.01); *G08B 25/002* (2013.01); *G08B 25/008* (2013.01); *G08B 25/012* (2013.01); *G08B 29/02* (2013.01); *G08B 29/04* (2013.01); *G08B 29/185* (2013.01); *G08B 29/22* (2013.01); *G08B 29/26* (2013.01); *H04L 12/282* (2013.01); *H04L 12/2803* (2013.01); *H04L 12/2809* (2013.01); *H04L 12/2818* (2013.01); *H04L 67/10* (2013.01); *H04L 67/24* (2013.01); *H04M 1/72561* (2013.01); *H04N 7/183* (2013.01); *H05B 33/0854* (2013.01); *H05B 33/0872* (2013.01); *H05B 37/0218* (2013.01); *H05B 37/0272* (2013.01); *F24F 11/46* (2018.01); *F24F 11/58* (2018.01); *F24F 11/70* (2018.01); *F24F 11/75* (2018.01); *F24F 11/89* (2018.01); *F24F 2120/10* (2018.01); *G08B 19/005* (2013.01); *G08B 25/08* (2013.01); *H04L 67/025* (2013.01); *Y02A 50/243* (2018.01)

(58) Field of Classification Search
CPC .... G08B 21/182; G08B 17/117; G08B 21/12; G08B 17/10; G08B 17/107; G01N 33/0031; G01N 33/004
See application file for complete search history.

(56) References Cited

U.S. PATENT DOCUMENTS

| | | | |
|---|---|---|---|
| 2003/0179096 A1* | 9/2003 | Hanan | G08B 3/10 340/628 |
| 2003/0234725 A1* | 12/2003 | Lemelson | G08B 7/066 340/521 |
| 2004/0140892 A1 | 7/2004 | Hanood | |
| 2005/0253709 A1* | 11/2005 | Baker | G08B 25/009 340/539.26 |
| 2008/0291037 A1 | 11/2008 | Lax | |
| 2010/0271220 A1* | 10/2010 | Pattok | G08B 3/10 340/628 |
| 2012/0126975 A1 | 5/2012 | Gonzales | |
| 2013/0008787 A1 | 1/2013 | Mammoto et al. | |
| 2013/0093594 A1* | 4/2013 | Brigham | G08B 17/107 340/628 |
| 2014/0085093 A1* | 3/2014 | Mittleman | H04L 12/282 340/628 |
| 2015/0054652 A1* | 2/2015 | Crochet | G08B 5/36 340/815.4 |
| 2015/0077737 A1* | 3/2015 | Belinsky | G01N 15/0211 356/51 |

* cited by examiner

| Color | Pulse ◎ | Rotate ↻ | Wave | Shimmer | On/Off ◉ |
|---|---|---|---|---|---|
| 601 | Alarm or test | | | | |
| 602 | Heads Up | Battery Low<br>Battery Critical | | | |
| 603 | Lights out (no problems) | Connected to client<br>Test completed (all OK)<br>Post-alarm (All Right) | | | |
| 604 | Choose Language<br>Button Pressed<br>Doorbell<br>Lights out (problems exist) | Ready for connections<br>Countdown to test<br>Reset<br>Shutdown begin<br>Shutdown countdown | Problem Description | Starting up | |
| 605 | | | | | Night Light / "Conditional Lighting" 606 |

SMART DEVICE WITH INTEGRATED CONDITIONAL LIGHTING

CROSS REFERENCES

This application is a continuation of U.S. Non-Provisional application Ser. No. 15/448,733, filed Mar. 3, 2017, entitled "Smart Device with Integrated Conditional Lighting," which is a continuation of U.S. Non-Provisional application Ser. No. 14/508,302, filed Oct. 7, 2014, entitled "Smart Home Device with Integrated Conditional Lighting," now U.S. Pat. No. 9,646,480, which claims priority to U.S. Provisional Application No. 61/887,969, filed Oct. 7, 2013 entitled "User-Friendly Detection Unit," and claims priority to U.S. Provisional Application No. 61/887,963, filed Oct. 7, 2013, entitled "Hazard Detection in a Smart-Sensored Home," which are each hereby incorporated by reference for all purposes.

BACKGROUND

Hazard detectors use sensors to detect substances in the air that may be harmful or that may indicate the development of a hazardous situation. For example, carbon monoxide (CO) and radon gas are substances that can be harmful to humans and animals if exposed to high amounts. However, these substances are difficult to detect with the human senses because they are colorless, odorless, and tasteless. A hazard detector can detect the presence of these substances and prevent the harmful effects of exposure by alarming to notify a user. In other instances, a substance such as smoke, while not necessarily harmful in and of itself, can indicate the development of a hazardous situation, such as fire. An early alarm of the presence of such a substance can prevent the hazardous situation from developing or minimize the harmful effects of the situation. Interconnected hazard detectors include detectors that are connected to a network, enabling communication between the detectors or with a central control unit. This provides several advantages over stand-alone detectors, including the ability to activate multiple alarms when a single detector is triggered. Hazard detectors may be certified under standards defined by governing bodies and/or by companies that perform safety testing, such as Underwriters Laboratories (UL). For example, certain UL standards define thresholds for when smoke detectors and CO detectors should sound an alarm. Certain UL standards also define the required characteristics of the alarm, such as powering requirements and the volume, pitch, and pattern of the alarming sound.

FIELD

This patent specification relates to systems, devices, methods, and related computer program products for smart buildings including the smart home. More particularly, this patent specification relates to detection units, such as hazard detection units (e.g., smoke detectors. carbon monoxide sensors, etc.) or other monitoring devices, that are useful in smart building and smart home environments.

SUMMARY

Various methods, systems, devices, apparatuses, and computer-readable mediums are presented. Such embodiments may involve a hazard detector that has an on-board light. The light may be activated based on a user being present in the vicinity of the hazard detector and the brightness level in the ambient environment being less than a threshold level. Other factors, such as a battery charge level and whether a hazard has been detected may be considered when determining whether the light should be illuminated. The light may serve multiple purposes, one of which being to output light when certain conditions are realized.

In some embodiments, a hazard detector is presented. The hazard detector may include a hazard sensor that detects the presence of a hazardous condition in an ambient environment of the hazard detector, The hazard detector may include a light sensor that detects an ambient brightness level of the ambient environment of the hazard detector. The hazard detector may include a motion sensor that detects motion of a user in the ambient environment of the hazard detector. The hazard detector may include a light that is capable of outputting light into the ambient environment of the hazard detector. The hazard detector may include a processing system, the processing system being in communication with the hazard sensor, the motion sensor, the light sensor, and the light. The processing system may include at least one processor and may be configured to receive an indication of the ambient brightness level in the ambient environment of the hazard detector from the light sensor. The processing system may be configured to determine that the ambient brightness level is less than a threshold brightness value. The processing system may be configured to receive information from the motion sensor indicative of the user moving in the ambient environment of the hazard detector. The processing system may be configured to cause the light to illuminate based on the ambient brightness level being below the threshold brightness value and the user moving in the ambient environment of the hazard detector.

Embodiments of such a hazard detector may include one or more of the following features: The processing system may be configured to determine a charge level of one or more batteries of the hazard detector. The processing system may be configured to compare the determined charge level of the one or more batteries of the hazard detector to a threshold charge level, wherein the processing system being configured to cause the light to illuminate based on the ambient brightness level being below the threshold brightness value and the user being present in the ambient environment of the hazard detector is further based on the determined charge level being greater than the threshold charge level. The processing system may be configured to access a stored data structure that identifies a plurality of colors linked with a plurality of states of the hazard detector. The processing system may be configured to select a color for the light based on a state of the hazard detector using the stored data structure, wherein the state is indicative of the ambient brightness level being below the threshold brightness value and motion being present in the ambient environment of the hazard detector. The processing system may be configured to receive an indication of a type of room in which the hazard detector is or will be installed. The processing system may be configured to determine that the indication of the type of room is indicative of a room type other than a bedroom, wherein the processing system being configured to activate the light based on the ambient brightness level being below the threshold brightness value and motion being present in the ambient environment of the hazard detector comprises the processing system being configured to cause the light to illuminate based on the ambient brightness level being below the threshold brightness value, motion being present in the ambient environment of the hazard detector, and the received indication of the type of room being indicative of a room type other than a bedroom. The hazard detector may include a wireless communication interface in communication with the processing system. The processing system may be further configured to perform an initial configuration of the hazard detector using a wireless connection using the hazard detector and a computerized wireless device that is in communication with the hazard detector.

Additionally or alternatively, embodiments of such a hazard detector may include one or more of the following features: The processing system may be configured to enable a path-light (or night-light) feature based at least in part on the initial configuration of the hazard detector being performed via the wireless connection using the hazard detector and the computerized wireless device. The processing system being configured to activate the light based on the ambient brightness level being below the threshold brightness value and motion being present in the ambient environment of the hazard detector may include the processing system being configured to activate the light based on the ambient brightness level being below the threshold brightness value, motion being present in the ambient environment of the hazard detector, and the path-light feature being enabled based at least in part on the initial configuration of the hazard detector being performed via the wireless connection using the hazard detector and the computerized wireless device. The light may be comprised of a plurality of light emitting diodes (LEDs) and the light outputs light from the hazard detector in a shape of a ring when each of the plurality of LEDs is illuminated. The hazard detector may include a wireless communication interface in communication with the processing system. The processing system may be configured to receive, from a remote server, via a wireless network, a message indicative that a path-light feature has been disabled by a user via a remote computerized device. The processing system may be configured to disable the path-light feature such that the light remains unlit in response to the ambient brightness level being below the threshold brightness value and motion being present in the ambient environment of the hazard detector. The hazard detector may include a wireless communication interface in communication with the processing system. The processing system may be further configured to receive, from a remote server, via a wireless network, a message indicative that a brightness level of a path-light feature has been set to a user-defined brightness level. The processing system may be configured to illuminate the light at the user-defined brightness level based on the ambient brightness level being below the threshold brightness value and motion being present in the ambient environment of the hazard detector. The light may be capable of illuminating a plurality of colors. The processing system being configured to activate the light based on the ambient brightness level being below the threshold brightness value and the presence in the ambient environment of the hazard detector may include the processing system being configured to cause the light to illuminate a first color of the plurality of colors. The processing system may be configured to receive an indication of the presence of the hazardous condition from the hazard sensor. The processing system may be configured to activate the light in response to receiving the presence of the hazardous condition from the hazard sensor, wherein the light is illuminated a second color of the plurality of colors.

In some embodiments, a hazard detector apparatus for providing conditional lighting by a hazard detector may be presented. The apparatus may include means for measuring an ambient brightness level in an ambient environment of the hazard detector. The apparatus may include means for determining that the ambient brightness level is less than a threshold brightness value. The apparatus may include means for collecting motion data indicative of a user moving in the ambient environment of the hazard detector. The apparatus may include means for illuminating a light of the hazard detector based on the ambient brightness level being below the threshold brightness value and the user moving in the ambient environment of the apparatus.

In some embodiments, a method for providing conditional lighting by a hazard detector may be presented. The method may include measuring, by the hazard detector, an ambient brightness level in an ambient environment of the hazard detector. The method may include determining, by the hazard detector, that the ambient brightness level is less than a threshold brightness value. The method may include collecting, by the hazard detector, motion data indicative of a user moving in the ambient environment of the hazard detector. The method may include illuminating, by the hazard detector, a light of the hazard detector based on the ambient brightness level being below the threshold brightness value and the user moving in the ambient environment of the hazard detector. Such a method may be implemented using a non-transitory processor-readable medium such that one or more processors perform instructions that cause the steps of the method to occur.

BRIEF DESCRIPTION OF THE DRAWINGS

FIG. 6 illustrates various combinations of visual effects and color that may be used by a hazard detector.

DETAILED DESCRIPTION

Hazard detectors, such as smoke alarms and carbon monoxide detectors, may be installed in multiple locations within a home (or other form of structure). For example, a typical home may have a hazard detector in each bedroom, a living room, the dining room, and a hallway. It may be useful to occupants of such home for the hazard detectors to provide functionality in addition to detecting hazards. As detailed herein, when a hazard is not being detected, the hazard detector may provide ancillary benefits to the home occupants. The hazard detector may function to provide conditional lighting, which may also be referred to as a "path light" feature.

Such conditional lighting may involve the hazard detector outputting light when certain conditions are present in the ambient environment of the hazard detector. For instance, when the ambient environment of the hazard detector is darkened and motion is detected, the hazard detector may be configured to activate its light and output an amount of light, which may be sufficient to illuminate the ambient environment for a person to see nearby objects. In some embodiments, if a household's electrical system is connected to the hazard detector, the light may be activated whenever the ambient environment of the hazard detector is determined to be darker than a threshold brightness value. In addition to such lighting being conditional on motion and/or a darkened environment, if the hazard detector was installed in a bedroom, the conditional lighting feature may be disabled or may default to being disabled. It may be unlikely that a user would want such conditional lighting in a bedroom because small nocturnal movements, such as rolling over in bed, may trigger the conditional lighting of the hazard detector to activate. The output of conditional lighting by a hazard detector may be contingent on a hazardous situation not being detected. If at any time, such as when the conditional lighting is active or inactive, the hazard detector (or another hazard detector in communication with the hazard detector) detects a hazardous situation, the conditional lighting feature may be disabled and light and/or sound associated with the detected hazardous situation may be output, such as until the hazardous situation is no longer detected.

The light of the hazard detector may serve multiple purposes. For instance, the light may also be used to output status indications to the user in addition to providing conditional lighting. The color and/or animation output by the light when providing conditional lighting may be unassociated with a status indication, such as to prevent a user from becoming confused as to whether the light is indicating a status or is outputting conditional lighting. For instance, white light may be output by the hazard detector as conditional lighting to illuminate the ambient environment, while each status is associated with a color other than white.

Figure 1:
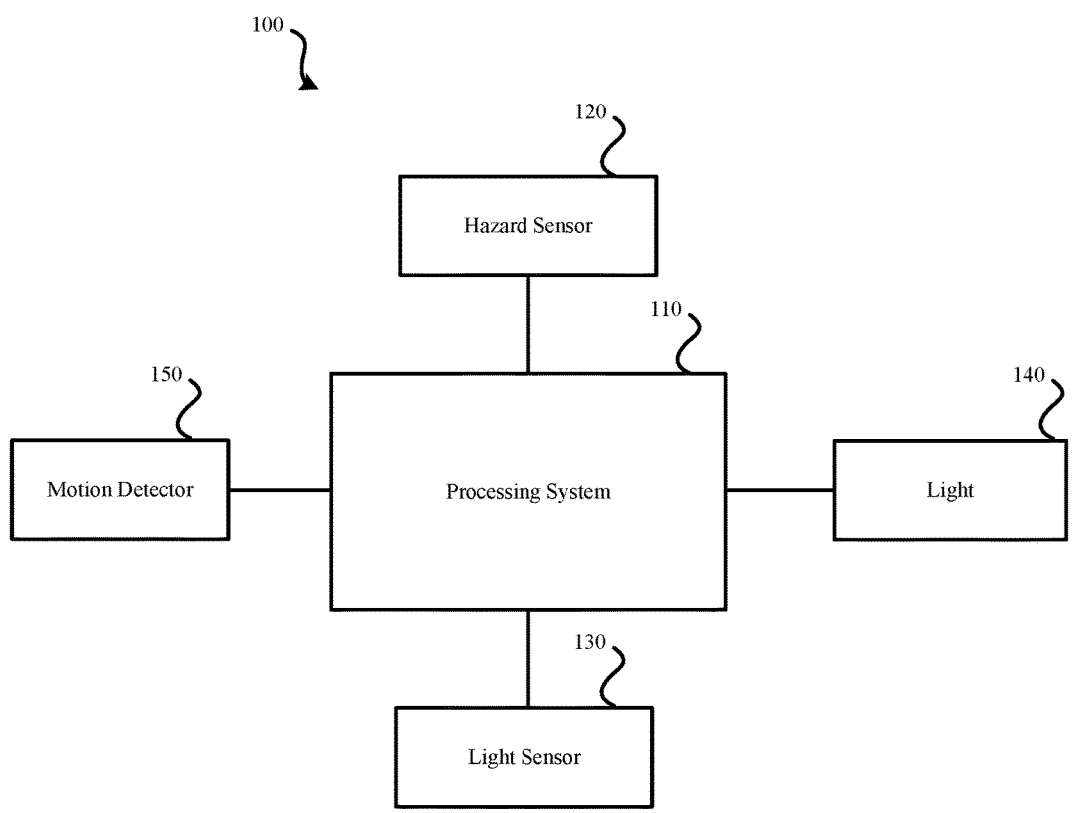
FIG. 1 illustrates an embodiment of a hazard detector that provides lighting based on certain conditions being present in the ambient environment of the hazard detector.

FIG. 1 illustrates an embodiment of a hazard detector 100 that provides lighting based on certain conditions being present in the ambient environment of the hazard detector. Hazard detector 100 may include: processing system 110, hazard sensor 120, light sensor 130, light 140, and presence detector 150. It should be understood that additional components may be present and are not illustrated for simplicity of understanding. For instance, hazard detector 100 may include one or more power sources and a case to house components of the hazard detector.

Processing system 110 may include one or more processors. Processing system 110 may receive input from hazard sensor 120, light sensor 130, presence detector 150, and/or other sources. Based on input from hazard sensor 120, light sensor 130, presence detector 150, and/or other sources, processing system 110 may cause light 140 to illuminate using various illumination modes. In some embodiments, processing system 110 includes at least two processors: a low-level processor and a high-level processor. The low-level processor may handle functions related to hazard detection and may be communicatively connected with hazard sensor 120. A high-level processor, which may be configured to handle functions related to user input, wireless communication, and usability may control illumination of light 140. In some embodiments, both the high and low level processors are able to cause light 140 to illuminate. Such processing may be divided between the high and low level processor such that functions of processor system 110 related to hazard detection are substantially isolated from other functions directed to usability. For instance, the low level processor may be able to cause an alarm to sound if a hazardous condition is present even if the high level processor is not functioning properly.

Hazard sensor 120 may represent a smoke sensor or a carbon monoxide sensor that detects the presence of smoke or carbon monoxide, respectively, in the ambient environment of the hazard detector. In other embodiments, hazard sensor 120 may represent some other form of sensor that detects a hazard in the ambient environment of hazard detector 100. While a single hazard sensor 120 is illustrated as present in hazard detector 100, it should be understood that in various embodiments multiple hazard sensors may be present, such as a carbon monoxide sensor and a smoke sensor. Further, multiple types of smoke sensors may be present, such as an ionization-based smoke sensor and a photoelectric-based smoke sensor. Hazard sensor 120 may be communicatively connected with processing system 110 such that, when a hazard is detected by hazard sensor 120, processing system 110 receives input from the sensor indicative of the hazard. In some embodiments, the low-level processor of processing system 110 receives the indication of the presence of the hazard.

Light sensor 130 detects the presence of light in the ambient environment of hazard detector 100. Light sensor 130 may detect a brightness level in the ambient environment of hazard detector 100. Such a brightness level may be affected by natural and artificial lighting. Light sensor 130 may provide an indication of the brightness level in the ambient environment of hazard detector 100 to processing system 110.

Light 140 may represent a light integrated into hazard detector 100 that outputs light to the external environment around hazard detector 100. Light 140 may be controlled by processing system 110. Light 140 may include one or more lighting elements, such as light emitting diodes (LEDs). Light 140 may be capable of outputting various illumination modes that can include: multiple colors, multiple animation patterns, and/or such multiple animation patterns at varying speeds. The at least one color, animation pattern, and speed of animation output by light 140 may be determined based on a determination performed by processing system 110. Therefore, based on conditions monitored by processing system 110, light 140 may be illuminated or disabled. When light 140 is illuminated, the one or more colors, animation pattern, and/or speed of the animation output by light 140 may vary based on a determination performed by processing system 110.

Presence detector 150 may detect a presence or motion within the ambient environment of hazard detector 100. Presence detector 150 may include one or more passive infrared (PIR) sensors and/or ultrasonic sensors that receive infrared radiation (or reflected ultrasonic sound) from the ambient environment of the hazard detector. For instance, a user walking in the vicinity of hazard detector 100 emits infrared radiation which may be detected based on motion by presence detector 150. In other embodiments, presence detector 150 may additionally or alternatively use some other form of sensor than a PIR sensor, such as an ultrasonic sensor. Presence detector 150 may provide an indication to processing system 110 of when motion is present in the ambient environment of hazard detector 100. Generally, presence detector 150 may be a form of sensor that can detect a user's presence even if motionless, such as based on an infrared signature of the user or a captured image. In some embodiments, presence detector 150 outputs raw data that is analyzed by processing system 110 to determine if motion is present. In some embodiments, motion may be analyzed to determine if it likely corresponds to a person or is incidental (e.g., a pet, an object being warmed by sunlight, etc.).

Figure 2:
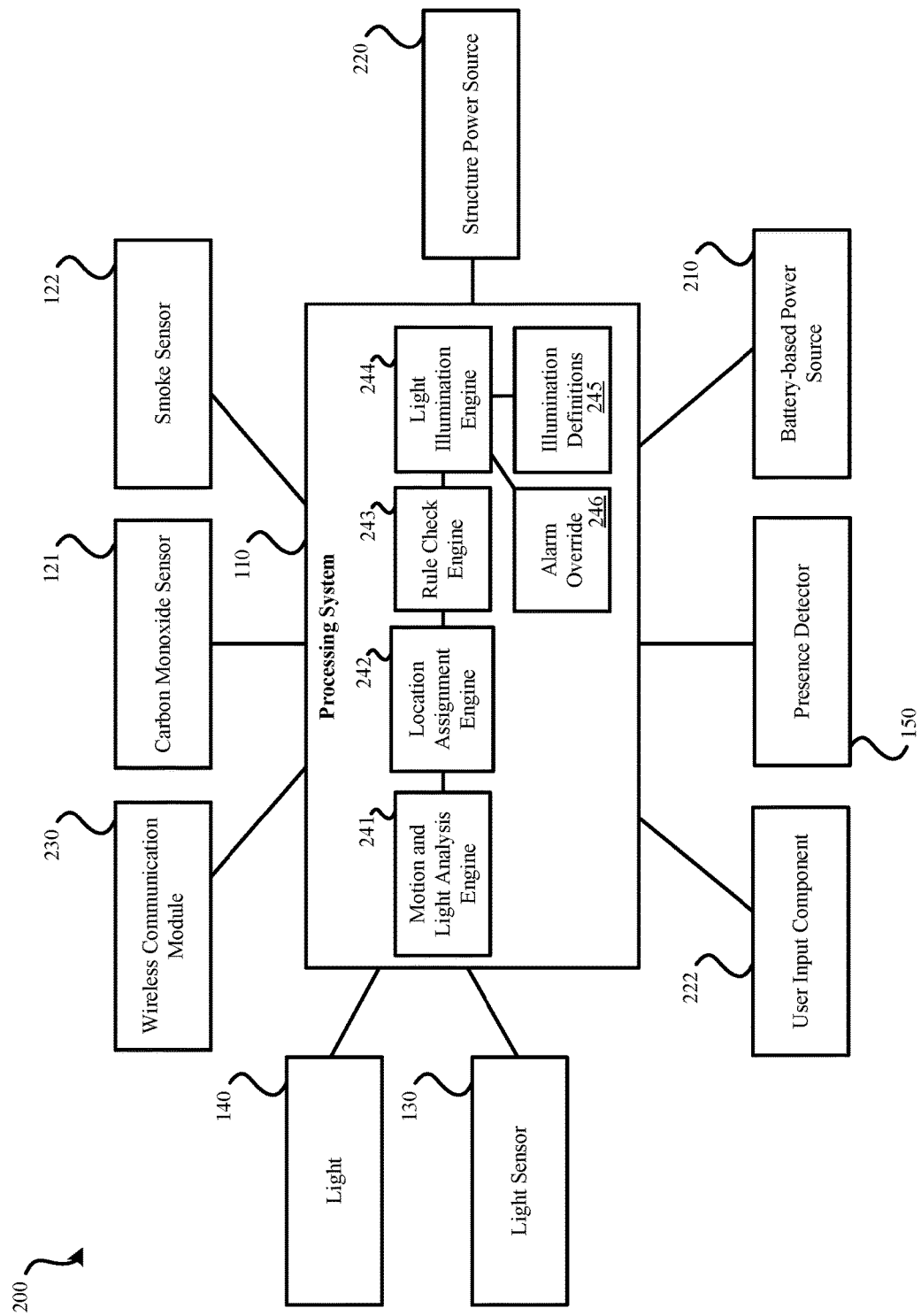
FIG. 2 illustrates another embodiment of a hazard detector that provides lighting based on certain conditions being present in the ambient environment of the hazard detector.

It should be understood that the block diagram presented in hazard detector 100 in FIG. 1 is highly simplified. As such, components that are not illustrated may be present, such as a power source, case, light guide, etc. FIG. 2 illustrates an embodiment of a hazard detector 200 that provides lighting based on certain conditions being present in the ambient environment of the hazard detector. Hazard detector 200 may represent a more detailed embodiment of hazard detector 100 of FIG. 1. In hazard detector 200, various components may be present including: processing system 110, light sensor 130, light 140, carbon monoxide sensor 121, smoke sensor 122, battery-based power source 210, wireless communication module 230, user input component 222, structure power source 220, and presence detector 150.

Processing system 110 of hazard detector 200 may include multiple submodules. Such submodules may be implemented using hardware, firmware, and/or software that is executed by underlying hardware, such as one or more processors. Such modules may include: motion and light analysis engine 241, location assignment engine 242, rule check engine 243, light illumination engine 244, illumination definitions 245, and alarm override 246. For instance, such modules may represent code that is executed by a high-level processor and/or a low-level of hazard detector 200.

Motion and light analysis engine 241 may receive input from light sensor 130 and presence detector 150. Light sensor 130 may provide motion and light analysis engine 241 with an indication of a brightness level of the ambient environment of hazard detector 200. Motion and light analysis engine 241 may compare this received brightness level to a stored brightness threshold value, such as to determine if the brightness in the ambient environment of the hazard detector has become darkened (the received brightness level is equal to or less than the threshold value). Presence detector 150 may provide motion and light analysis engine 241 with an indication of whether or not motion has been detected in the ambient environment of the hazard detector. In some embodiments, presence detector 150 provides motion and light analysis engine 241 with the raw motion data that is analyzed by motion and light analysis engine 241 to determine if a user is present in the ambient environment of hazard detector 200, such as based on motion.

Location assignment engine 242 may determine a room type in which hazard detector 200 has been installed. In some embodiments, such as during an initial configuration or set up, a user may specify a type of room in which hazard detector 200 is installed. Location assignment engine 242 may maintain an indication of the type of room indicated by the user and may use this indication to determine whether conditional lighting should be provided. For example, by default, conditional lighting may be disabled for hazard detectors that are installed within a bedroom. Some or all other room types, by default, may have conditional lighting enabled. Conditional lighting may be disabled for bedrooms so that incidental movement, such as during sleep, does not trigger the light on hazard detector 200 to illuminate. A user, during setup by accessing a user account maintained by a remote server, may alter the default enablement setting for conditional lighting based on the room type.

Rule check engine 243 may be configured to check various rules to determine if conditional lighting is eligible to be illuminated. For example, one possible rule, that may be checked before conditional lighting is enabled, may be to determine whether an initial configuration of hazard detector 200 was performed using wireless communication module 230 and a wireless communication device. Another possible rule that may be checked before conditional lighting is illuminated is whether a user has reconfigured hazard detector 200 to alter whether conditional lighting is enabled or disabled. In some embodiments, a user may provide such a preference via a user account maintained by a remote server. Periodically, processing system 110 may communicate with such a remote server via wireless communication module 230. During such a communication session, the user preference may be loaded to processing system 110 such that conditional lighting occurs in compliance with the user preference.

Light 140 and light sensor 130 may function as detailed in relation to hazard detector 100. In hazard detector 200, two hazard sensors are present: carbon monoxide sensor 121 and smoke sensor 122. In some embodiments, multiple versions of each of these types of sensors can be present. For instance, an ionization and a photoelectric smoke sensor may be present in hazard detector 200. When carbon monoxide sensor 121 senses carbon monoxide or smoke sensor 122 senses smoke, an indication may be sent to a processor of processing system 110, which may be handled by alarm override 246 if conditional lighting is active. An indication of an alarm condition may be transmitted to a low-level processor that triggers an alarm to sound and/or a light color and/or animation to be output by light 140. This low-level processor may trigger light 140 directly to illuminate in a state indicative of a hazard or may provide input to a high-level processor that is part of processing system 110 that triggers a lookup of an illumination definition via stored illumination definitions 245 to determine an appropriate color, animation, and/or speed of animation to use for illumination of light 140. Regardless of whether the high-level or low-level processor is used, a different color, animation, and/or speed may be used for carbon monoxide as compared to smoke. In some embodiments, both the low and high level processors are capable of causing light 140 to illuminate.

Light illumination engine 244 may control illuminating light 140. If light analysis engine 241 provides information to light illumination engine 244 indicative of the brightness level in the ambient environment of hazard detector 200 being below a threshold value and motion being present in the ambient environment, light illumination engine 244 may cause light 140 to illuminate. Light illumination engine 244 causing light 140 to illuminate may be conditioned on location assignment engine 240 determining that hazard detector 200 is not installed within a bedroom. Light illumination engine 244 causing light 140 to illuminate may also be conditioned on rule check engine 243 determining that one or more evaluated rules indicate that conditional lighting is eligible to be illuminated.

Light illumination engine 244 may illuminate light 140 under various conditions in addition to providing conditional lighting based on motion and a darkened environment. Light illumination engine 244 may access illumination definitions 245 to determine what color and/or animation should be used to illuminate light 140 based on the observed conditions by motion and light analysis engine 241. Illumination definitions 245 may be a stored set of definitions that define one or more colors and/or one or more animations used to illuminate light 140 in certain situations. Such illumination definitions 245 may be stored on a non-transitory processor readable medium that is part of processing system 110 or maintained separately. In some embodiments, in order to provide the nightlight feature, light illumination engine 244 may access illumination definitions 245 to determine that the light should be illuminated white and an animation that involves fading on and fading off should be used for initiating and ending illumination of light 140. Illumination definitions 245 may store definitions of other conditions of hazard detector 200. For instance, light 140 may be illuminated a different color and a user different animation if a hazard is detected by carbon monoxide sensor 121 or smoke sensor 122.

Light illumination engine 244 may cause light 140 to illuminate while motion is being detected by motion and light analysis engine 241 and the brightness level in the ambient environment of hazard detector 200 remains below the threshold as analyzed by motion and light analysis engine 241. During this time, it is possible that carbon monoxide sensor 121 and/or smoke sensor 122 may determine that a hazard is present in the ambient environment of hazard detector 200. In such a situation, alarm override 246 may cause conditional lighting, which may involve white light being output by light 140 to cease being output. Instead, alarm override 246 may cause a color and animation associated with the detected hazard to be output by light 140. Additionally, sound may be being output by a speaker, such as shrill alarm sound used to alert the user to imminent danger.

Wireless communication module 230 may allow processing system 110 to communicate with a wireless network present within the structure in which hazard detector 200 is installed. For instance, wireless communication module 230 may communicate with a wireless network that uses the IEEE 802.11a/b/g network protocol standard for communication. Wireless communication module 230 may permit processing system 110 to communicate with a remote server, which may be maintained by a manufacturer of hazard detector 200 or by a third-party. The remote server may be configured to provide information to processing system 110 about an account of a user associated with hazard detector 200. Periodically, such as once a day or once an hour, the wireless communication module 230 may be configured to query a remote server regarding the status of a user account associated with the hazard detector. For instance, if an account of the user maintained at the remote server requires attention from a user, such indication may be provided to processing system 110 via wireless communication module 230 in response to such a query. Further, processing system 110 may transmit status information to a remote server. Such an arrangement may permit a user to view status information about the hazard detector by logging in to the remote server via a computing device and accessing the user account.

Wireless communication module 230 may also permit direct connection with a wireless computerized device. For instance, wireless communication module 230 may create a wireless area network (e.g., WiFi network) that a computerized wireless device, such as a tablet computer or smartphone, can connect with. Once connected, messages may be exchanged between processing system 110 (via wireless communication module 230) and a wireless computerized device, such as to permit an initial configuration of hazard detector 200 to be performed via the computerized wireless device. In other embodiments, such an initial configuration is performed via a network connection through a router or other form of direct communication, such as Bluetooth®) or WiFi Direct®. More generally, the required data communications can be carried out using one or more of a variety of custom or standard wireless protocols (e.g., cellular, 3G/4G, Wi-Fi, ZigBee, 6LoWPAN, BLE, etc.) and/or any of a variety of custom or standard wired protocols (CAT6 Ethernet, HomePlug, etc.). One particularly useful protocol that can be used is the Thread protocol, which is promulgated by the Thread Group and based on 802.15.4, IETF IPv6, and 6LoWPAN. For some embodiments, devices that are powered by the household mains current, either directly or through an AC power adapter, can be provided with a combination of Wi-Fi, which can be relatively power-intensive, along with one or more lower-power protocols such as Thread and/or BLE. In contrast, devices that are power-constrained in that they are not powered by the household mains current and do not have access to a high-capacity battery source are provided only with one or more low-power protocols such as Thread and/or BLE. In some cases, devices that are not powered by the household mains current, but do have access to a reasonably high-capacity battery source, can be provided with a combination of Wi-Fi and one or more lower-power protocols such as Thread and/or BLE, with the Wi-Fi communications being controlled to be temporally restricted, such as being turned on only during brief periodic time intervals (e.g., once per day to upload logs and receive updates from the cloud), during particular device-sensed events, or when the user has physically actuated the device such as by pressing a button on the device. The hazard detectors described herein can be provided in two different SKUs, one SKU being mains-powered with battery backup and the other SKU being battery only, albeit with a relatively large battery source (e.g., six lithium AA cells). For this battery-only SKU, the hazard detector is preferably provided with a combination of the temporally restricted Wi-Fi and one or more lower-power protocols such as Thread and/or BLE.

Whether via a wireless computerized device or a remote server, a user may provide input to hazard detector 200 via wireless communication module 230 that is indicative of whether conditional lighting should be enabled and/or a desired brightness level of the conditional lighting. By default, conditional lighting may be enabled at a brightness level selected based on whether hazard detector 200 operates solely on batteries or receives power from a structure's wired power source. If the structure power source is available, the brightness level of the conditional lighting may, by default, be increased to provide better illumination. If batteries are used as the sole power source, the brightness level of the conditional lighting may, by default, be decreased to preserve battery life. In some embodiments, the brightness level is set, by default, to a same brightness level for battery and wired power source embodiments. Via the remote server, a user may update a preference indicative of a desired brightness level. When the hazard detector messages with the remote server, the brightness level provided by the user may be transmitted to hazard detector 200 via wireless communication module 230.

User input component 222 may represent a component that receives input that can be passed to processing system 110. User input component 222 may take the form of a button or switch on hazard detector 200. By depressing the button or otherwise actuating user input component 222, a user can provide input via user input component 222 to processing system 110. For instance, user input component 222 may be used by a user to disable an alarm being sounded by hazard detector 200. User input component 222 may be encircled or have its perimeter otherwise outlined by light 140 (that is, by the light itself and/or by light output by light 140). Therefore, when light 140 is active, and the user desires to provide input, the user may touch or push hazard detector 200 within the area defined by light 140 and/or the light output by light 140.

Presence detector 150 may detect the presence of a user in the vicinity of hazard detector 200 and may function as detailed in relation to FIG. 1. Presence detector 150 may include one or more sensors, such as passive infrared (PIR) sensors. Presence detector 150 may detect the presence of one or more users, such as based on motion observed based on received infrared light. For instance, presence detector 150 may detect a wave gesture performed by a user. In some embodiments, presence detector 150 may only be enabled at certain times, which may conserve power. Such motion detection may be used to enable lighting to allow a user to see in the vicinity of hazard detector 200 and/or may be used to control and/or provide occupancy data to HVAC systems within the structure. Presence detector 150 may be integrated with user input component 222 such that user input component 222 conceals presence detector 150 within hazard detector 200. Further, an integrated lens may be present in user input component 222 such that presence detector 150 detects the presence of one or more users through the button of user input component 222.

Hazard detector 200 may include battery-based power source 210 and structure power source 220. Structure power source 220 may be used to power hazard detector 200 when such power is available. Structure power source 220 may represent a hard-wired connection within a structure (e.g., house, building, office, etc.) that provides an AC or DC power to one or more hazard detectors located throughout the structure. While the AC or DC power may be available a significant percentage of time (e.g., 99.5% of the time), it may be desirable for hazard detector 200 to continue functioning if structure power is unavailable (e.g., during a power failure). As such, battery-based power source 210 may also be present. Battery-based power source 210 may include one or more batteries (and/or may use one or more capacitors) which power the various components of hazard detector 200 when structure power source 220 is not available. In some embodiments of hazard detector 200, structure power source 220 is not present. As such, hazard detector 200 may permanently rely on battery-based power source 210 to power components of hazard detector 200. Structure power source 220 and battery-based power source 210 are illustrated in FIG. 2 as connected with processing system 110. It should be understood that, while structure power source 220 and battery-based power source 210 are illustrated as only connected with processing system 110, this is for simplicity of illustration only; structure power source 220 and/or battery-based power source 210 may be connected to the various components of hazard detector 200 as necessary to power such components.

Figure 3:
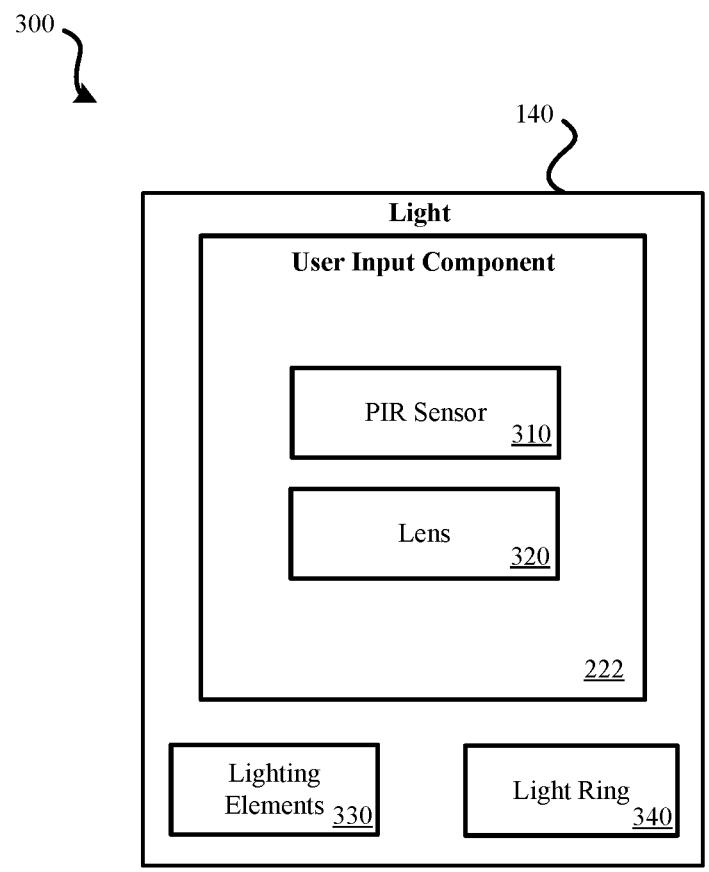
FIG. 3 illustrates an embodiment of a light configured to encircle a user input component of a hazard detector.

FIG. 3 illustrates an embodiment of a light configured to encircle a user input component of a hazard detector. Such a light may be used to provide conditional lighting as detailed in relation to FIGS. 1 and 2. Embodiment 300 may include light 140, user input component 222, PIR sensor 310, lens 320, lighting elements 330, and light ring 340. Light 140 may be understood as including lighting elements 330 and light ring 340. Lighting elements 330 may include one or more components that output light. For instance, lighting elements 330 may be LEDs. In some embodiments, light 140 includes five LEDs functioning as lighting elements 330. It should be understood that in other embodiments, a fewer or greater number of LEDs functioning as lighting elements 330 may be present.

Light 140, as illustrated embodiment 300, may encircle user input component 222. To accomplish this, light ring 340 may be used. Light ring 340, which, more generally, can be referred to as a light guide, may diffuse or otherwise direct light generated by lighting elements 330 to emanate a face of the hazard detector in which embodiment 300 is integrated. Light ring 340 may be a solid piece of transparent or semitransparent material, such as plastic or glass, that causes light emitted by lighting elements 330 to emanate from a hazard detector in approximately a continuous ring of light when all of lighting elements 330 are illuminated. As such, light ring 340 may cause output light to appear, from the exterior of the hazard detector of which embodiment 300 is a part, to be in the shape of a ring. This ring of light may be circular or oval. Other embodiments of light guides may cause output light to form some other form of perimeter, such as a perimeter of an octagon, quadrilateral, triangle, or some other geometric or abstract shape.

User input component 222, which may be in the form of a button, may be encircled by light output by light 140. More specifically, light output through light ring 340 and/or a portion of light ring 340 may substantially define the edge of user input component 222. As such, a user touching the hazard detector within a perimeter of light output by light ring 340 can be expected to be touching user input component 222. Such an arrangement may be particularly useful in the dark such that, when light is emanating from light ring 340, a user only needs to touch the hazard detector within the light output from light ring 340 in order to press user input component 222.

User input component 222 may be integrated with presence detector 150 as detailed in relation to hazard detector 200. In embodiment 300, PIR sensor 310 and lens 320 are being used as the presence sensor. PIR sensor 310 may sense the presence of a user based on infrared detection through the face of user input component 222. Incorporated as part of user input component 222 may be lens 320, which helps define a region in the environment of the hazard detector in which PIR sensor 310 can sense the presence of the user and/or a gesture being performed based on received infrared radiation.

Lighting elements 330 and at least a portion of light ring 340 may be located behind the face of user input component 222, similar to PIR sensor 310. As such, lighting elements 330 may generate light behind the face of user input component 222 and light ring 340 may direct such light to a portion of light ring 340 that is present on an exterior face of the hazard detector. Alternatively, light ring 340 may be completely or nearly completely hidden from external view behind user input component 222; light from lighting elements 330 may be directed by light ring 340 to reflect off of a portion of a case (or, more specifically, a cover plate) of the hazard detector, such as a portion of the case that is depressed. Such an arrangement may permit individual lighting elements of lighting elements 330 to not directly face the exterior of the hazard detector. Such an arrangement may be beneficial for space savings within the hazard detector, allowing for a compact configuration.

Figure 4:
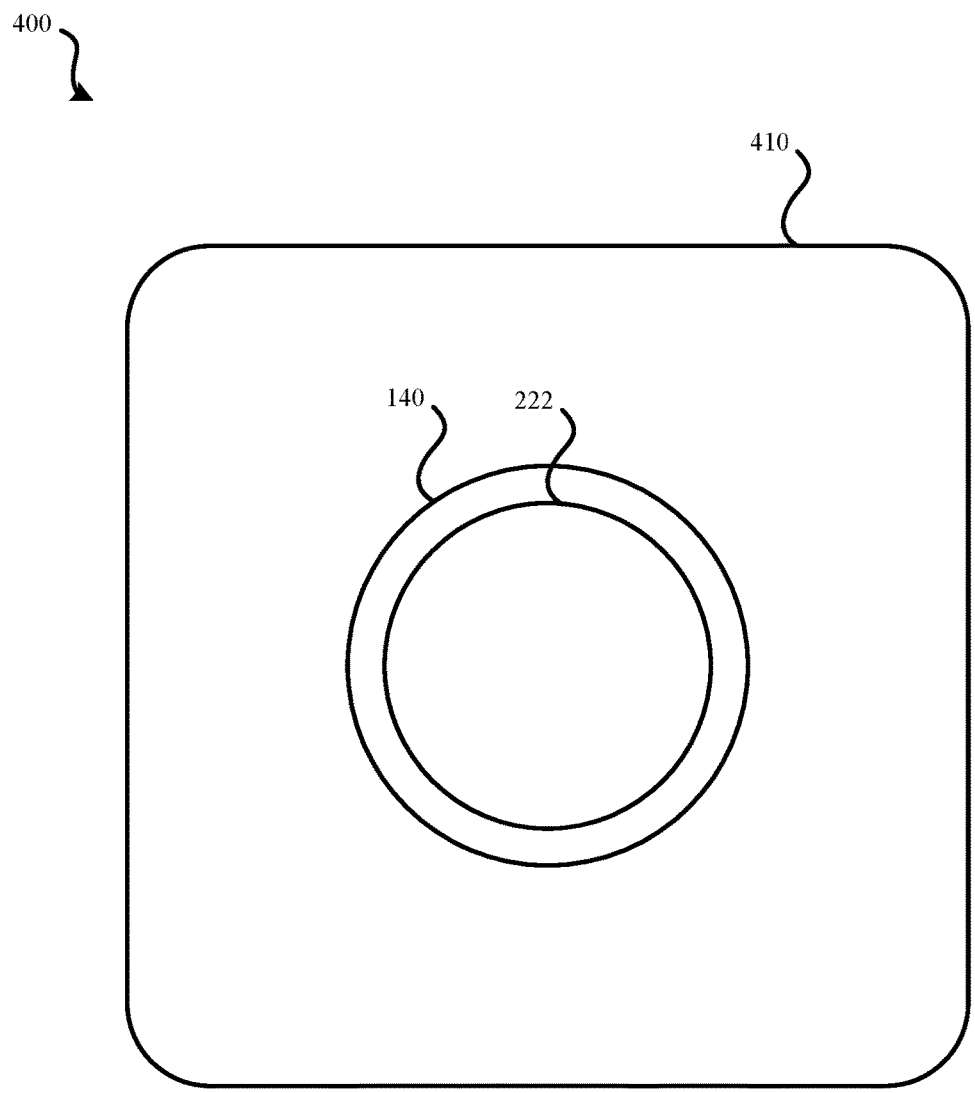
FIG. 4 illustrates an external view of an embodiment of a hazard detector with a ring-shaped light.

FIG. 4 illustrates an external view of an embodiment of a hazard detector 400 with a ring-shaped light. Hazard detector 400 may represent the hazard detectors of FIGS. 1 and 2, and may include the embodiment of FIG. 3. FIG. 4 illustrates an external view of an embodiment of a hazard detector 400. Hazard detector 400 may include case 410, light 140, and user input component 222. Case 410 may represent a shell of hazard detector 400 which is configured to be mounted to a wall or ceiling. Case 410 may allow airflow through hazard detector 400 to permit one or more sensors within hazard detector 400 to be exposed to the air of the ambient environment of hazard detector 400. On the side of case 410 opposite the side used for mounting to a wall or ceiling, light 140 may output light. The portion of light 140 visible in FIG. 4 may be a portion of a light ring that causes light generated by lighting elements hidden within the hazard detector to emanate from a face of case 410. In some embodiments light 140 is concealed within hazard detector 400, but a portion of case 410 (or some other physical portion of the hazard detector) is arranged to reflect light generated by light 140. For instance, a portion of case 410 may be depressed in order to reflect and scatter light output by light 140. Such a case may include a cover plate, front casing, backplate, and/or mounting plate. Light 140 may include one or more light elements, such as LEDs that are located within hazard detector 400 behind user input component 222.

While light 140 is illustrated as a ring (which can also be referred to as a halo), it should be understood that, in other embodiments of hazard detector 400, other shapes may be used for light 140. For instance, light 140 may be elliptical, square, triangular, some other geometric shape, some other abstract shape, or a line. Similarly, in some embodiments, case 410 is square or rectangular, with rounded edges. While such a design may be especially pleasing to the eye, other shapes, both geometric or abstract, may be used to house the functional components of hazard detector 400. Generation of the light may occur behind user input component 222 and may be directed by a light ring, which may also be located behind user input component 222, to emanate from the hazard detector in the appearance of a ring, as illustrated by the halo-like shape of light 140. As such, in some embodiments, the entire light ring and lighting elements (which, collectively, form light 140) may be located behind user input component 222 and the light directed by the light ring may reflect off of a recessed portion of case 410 into the ambient environment of hazard detector 400 for viewing by a user.

User input component 222 may include a lens that is used in conjunction with a presence sensor (e.g., PIR sensor) to determine if a user is present and/or detect whether a gesture has been performed by user. User input component 222 may have its perimeter substantially defined by the light emanating from light 140. User input component 222 may serve a dual function: functioning as a lens and as a button which can be pushed by user to provide input to hazard detector 400. In some embodiments, user input component 222 is a button but does not include an integrated lens. When user input component 222 is a button, by having user input component 222 encircled by emitted light by light 140, it may be easy for a user to locate the button in a darkened environment when light 140 is illuminated. In such a situation, the user would only need to push within the circle of light (the "halo") or other region defined by light 140 in order to actuate the button.

Light 140 may appear substantially centered on an exterior surface of case 410. Case 410 may be designed for a first exterior surface mount to a wall or ceiling. The opposite exterior surface of case 410 may include light 140. Light 140 and user input component 222 may be substantially centered about an axis extending through the center of the first and second exterior surfaces of case 410 of hazard detector 400. In other embodiments, light 140 and/or user input component 222 may not be centered on the exterior surface of case 410. In some embodiments, light 140 may not be recessed within case 410 or may extend beyond an exterior surface of case 410. For example, in some embodiments, light 140 may be present as a recessed portion of case 410 that permits light generated within case 410 (e.g., behind user input component 222) to emanate from the recessed portion of case 410.

In some embodiments, the location of light 140 is a depressed portion of case 410. From behind user input component 222 or from some other location within case 410, light is emitted into the depressed portion of case 410. The light reflects off of case 410 into the environment of hazard detector 400, outlining user input component 222. Further, due to the depressed portion of case 410, from various angles a user may be able to partially see behind user input component 222. Such a region may also be illuminated by light when light 140 is illuminated.

Figure 5:
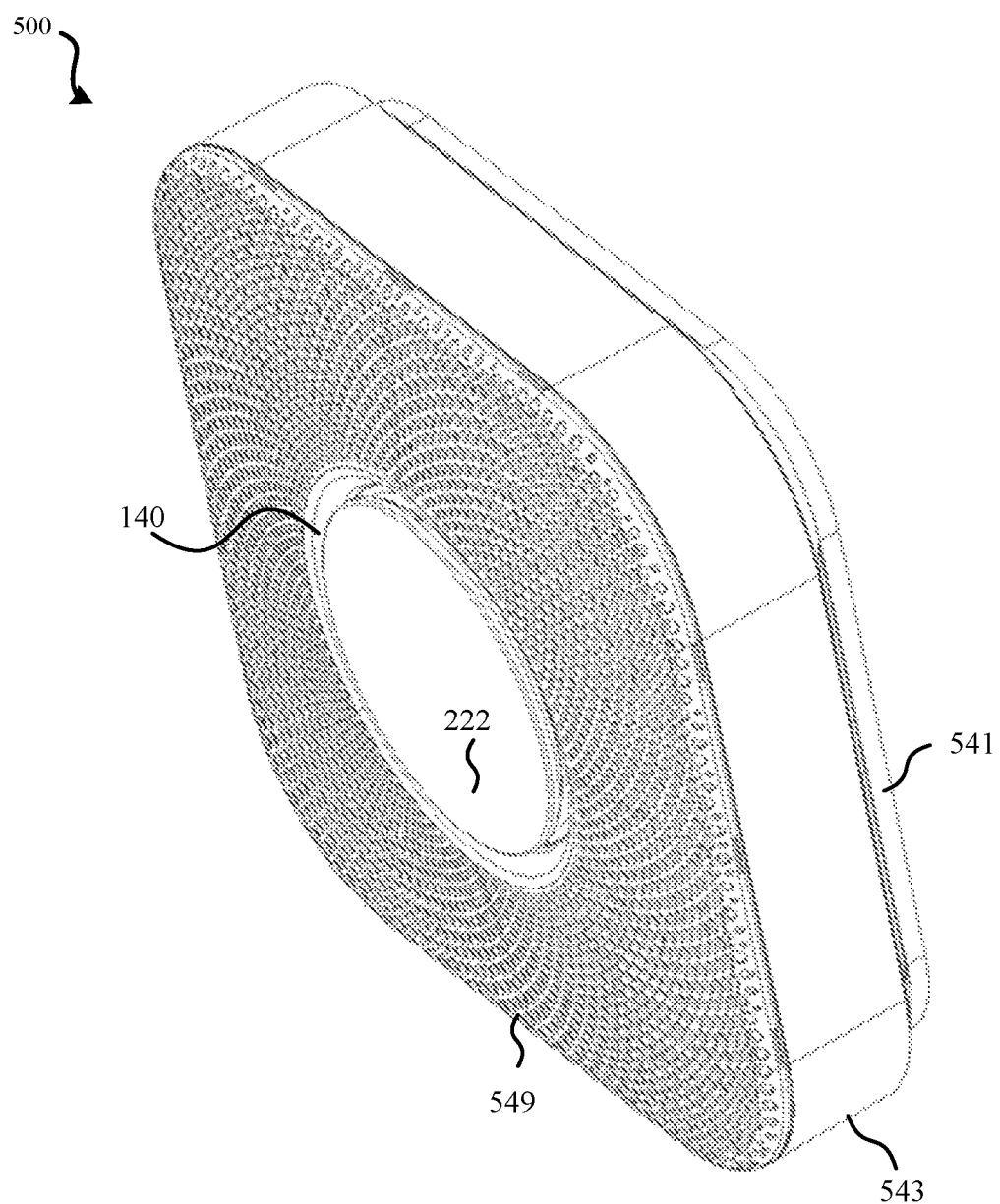
FIG. 5 illustrates an external view of an embodiment of a hazard detector that outputs a circular pattern of light.

FIG. 5 illustrates an embodiment of hazard detector 500 which may represent various embodiments of hazard detectors detailed in this document. Specifically, FIG. 5 shows mounting plate 541, front casing 543, and cover plate 549 in an assembled configuration with various other components, such as the hazard sensors and processing system, contained within an interior space of hazard detector 500. This figure also shows a plurality of holes or openings of cover plate 549 forming a visually pleasing design that is viewable by an occupant of a room within which the hazard detector 500 is mounted. The user input component 222 is shown attached to the hazard detector 500 so as to be centrally positioned with respect to cover plate 549.

FIG. 6 illustrates an embodiment 600 of various combinations of visual effects (also referred to as animations) and color that may be used by a hazard detector for illuminating a light, such as light 140 of FIGS. 1-5. Such combinations may be stored in the form of a look-up table by a hazard detector or may be accessible via a network from a remote computerized device, such as a cloud-based server system (e.g., cloud-computing system 1064). Based upon a status or condition of the hazard detector, the table of embodiment 600 may be used to determine a color and animation for illuminating the light. Color 601 may be red, color 602 may be yellow, color 603 may be green, color 604 may be blue, and color 605 may be white. Other color assignments are also possible. Definitions of colors, visual effects, and/or speeds may be stored by a hazard detector, such as in stored illumination definitions 245, which may be present on a non-transitory processor-readable medium. In response to a condition determined by the hazard detector, the processing system of the hazard detector may look up or otherwise determine the appropriate combination of colors, visual effect, and/or speed to use to illuminate the light. For example, if light illumination engine 244 determines that conditional lighting should be enabled based on factors including detected motion and the ambient environment of the hazard detector being darkened, entry 606 may be used to determine that the color to use for illumination of light 140 is white and a fade on/off animation should be used when initiating and ending illumination of light 140. Definitions of colors and animations may be provided to a user, such as in the form of a quick reference sheet or manual provided with a hazard detector when purchased.

Figure 7:
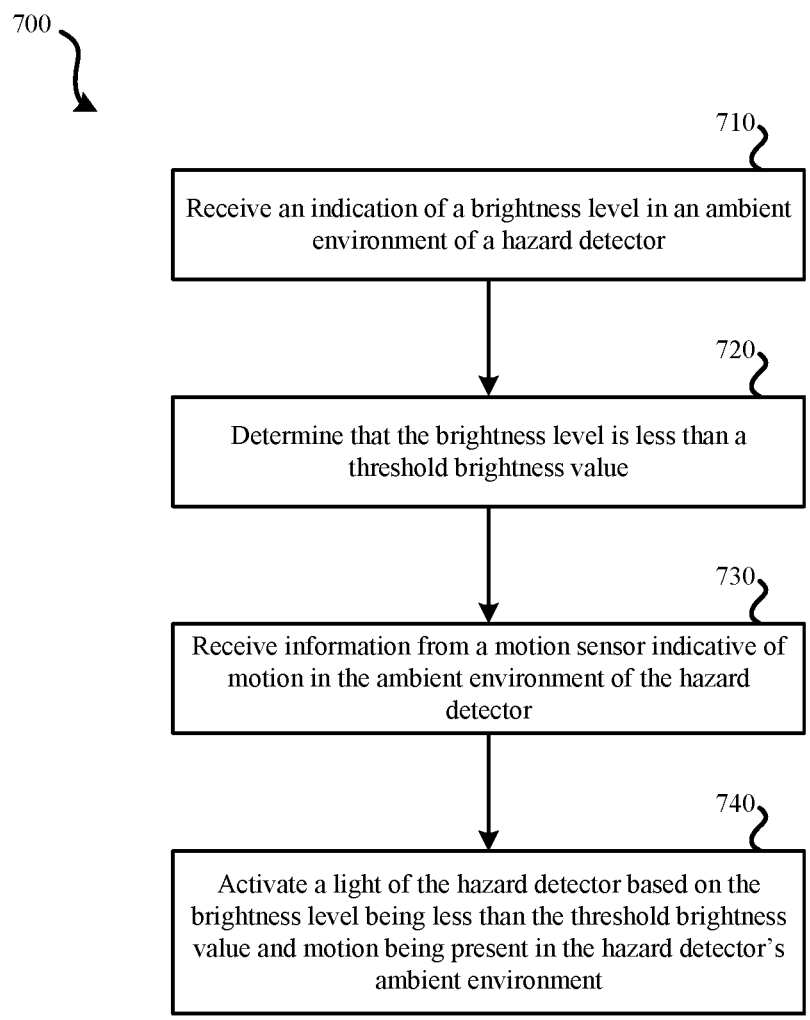
FIG. 7 illustrates an embodiment of a method for providing conditional lighting by a hazard detector.

The hazard detectors detailed in relation to FIGS. 1 through 5 and the illumination definitions detailed in relation FIG. 6 may be used to perform various methods. FIG. 7 illustrates an embodiment of a method 700 for providing conditional lighting by a hazard detector. Method 700 may be performed using any of the embodiments of hazard detectors detailed in relation to FIGS. 1 through 5. Further, it may be possible that other embodiments of hazard detectors may be used to perform the blocks of method 700. Each block of method 700 may be understood as generally being performed by a hazard detector or a component of the hazard detector.

At block 710, an indication of the brightness level in an ambient environment of a hazard detector may be received. Such an indication of the brightness in the ambient environment of the hazard detector may be received from a light sensor of the hazard detector by a processing system of the hazard detector. For instance, referring to hazard detector 200, light sensor 130 may provide an indication of the brightness level in the ambient environment of hazard detector 200 to processing system 110. Such indication may be provided periodically or may be provided by light sensor 130 to processing system 110 under specific circumstances. For instance, it may be possible that light sensor 130 may only monitor the brightness level in the ambient environment of hazard detector 200 when structure power source 220 supplies power to components of hazard detector 200.

At block 720, the brightness level received at block 710 may be compared to a stored threshold brightness value. Such a threshold brightness value may be used to determine whether the ambient environment of the hazard detector is darkened to an extent in which a nightlight feature of the hazard detector may be useful to users in the general vicinity. Referring to hazard detector 200, processing system 110 may compare the received brightness level from block 710 with the stored threshold brightness value to determine if the received brightness level from block 710 has decreased to less than the threshold brightness value. If not, method 700 may cease to be performed or may return to block 710. Therefore, in a brightness environment, blocks 710 and 720 may be repeatedly performed prior to block 730 being performed. Alternatively, in some embodiments block 730 may be performed before block 710 and/or block 720.

At block 730, information from a motion sensor of the hazard detector may be received by the hazard detectors processing system. Such information may be indicative of whether motion in the ambient environment of the hazard detector has been detected. In some embodiments, the motion sensor may analyze received infrared radiation to determine if a user is likely present in the ambient environment of the hazard detector. Such a motion sensor may provide an indication to a processing system of the hazard detector as to whether or not a user is likely present in the ambient environment of the hazard detector. In other embodiments, a motion sensor may provide raw data gathered by monitoring received infrared radiation to a processing system of the hazard detector. Such a processing system may in turn analyze such received data to determine if a user is likely present in the ambient environment of the hazard detector. Referring to hazard detector 200, presence detector 150 may provide data indicative of motion or presence of the user in the ambient environment of hazard detector 200 to processing system 110.

At block 740, a light of the hazard detector may be activated. Activation of the light may be contingent on motion being detected in the ambient environment of the hazard detector and the brightness level having been determined to be less than the threshold brightness value. As such, when illuminated, the light may serve as a nightlight when the room in which the hazard detector is installed is dark and motion has been detected. Because activation of the light is contingent on motion and a darkened environment, the nightlight feature is activated only when it is likely needed by a user. Following activation at block 740, method 700 may repeat until either the ambient environment of the hazard detector is no longer darker than the threshold brightness value or motion is no longer detected in the ambient environment of the hazard detector. At which time, the light of the hazard detector may cease illuminating for uses the nightlight feature. Activation of the light for such conditional lighting may use an animation to initiate (and, eventually conclude) illumination of the light, such as by fading the light on.

Figure 8:
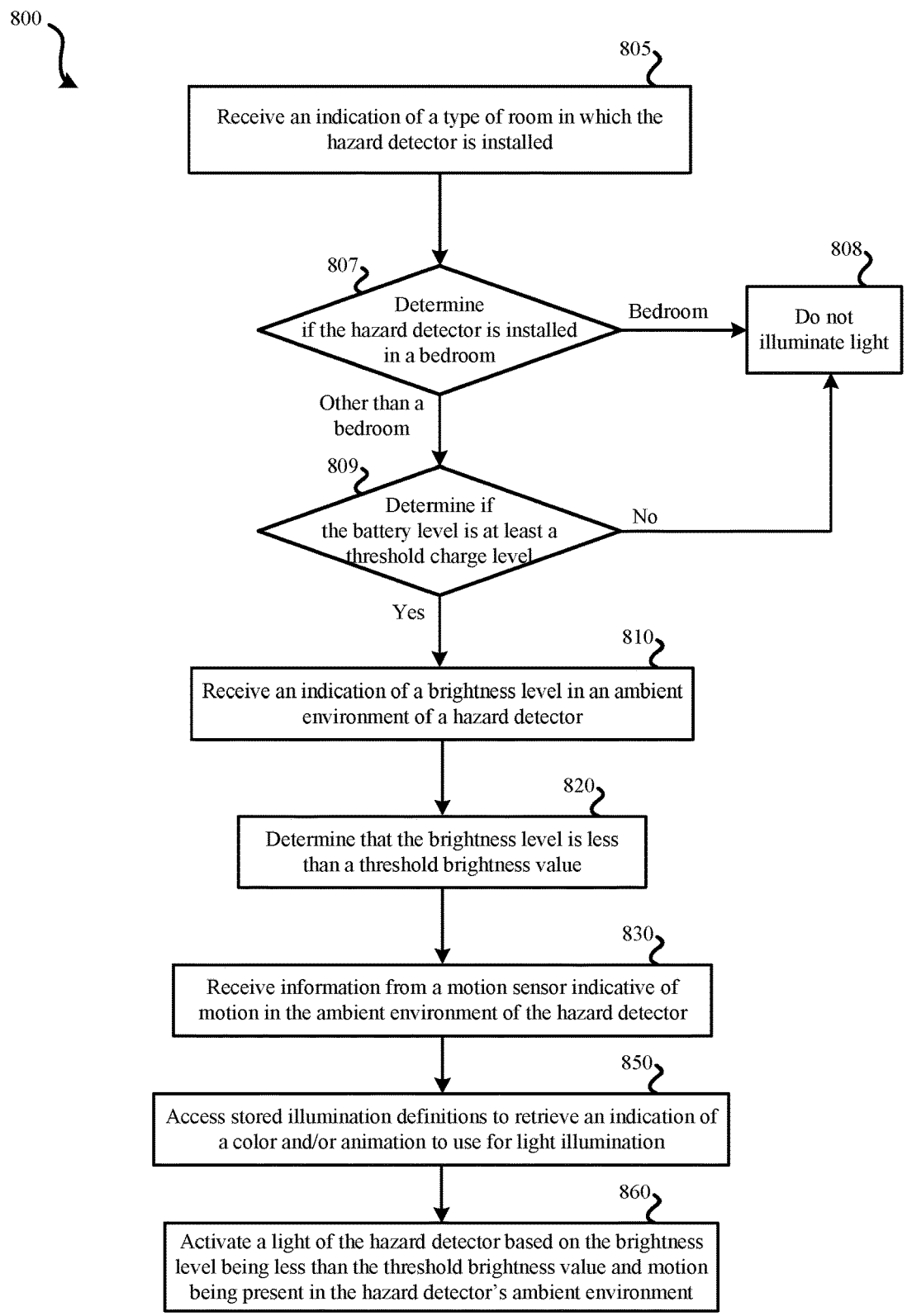
FIG. 8 illustrates an embodiment of a method for providing conditional lighting by a hazard detector contingent upon at least a location assignment.

FIG. 8 illustrates an embodiment of a method 800 for providing conditional lighting by a hazard detector contingent upon at least a location assignment. Method 800 may be performed using any of the embodiments of hazard detectors detailed in relation to FIGS. 1 through 5. Further, it may be possible that other embodiments of hazard detectors may be used to perform the blocks of method 800. Each block of method 800 may be understood as generally being performed by a hazard detector or a component of the hazard detector. Method 800 may represent a more detailed embodiment of method 700. As such, any or all blocks performed as part of method 700 may also be performed as part of method 800.

At block 805, the hazard detector may receive an indication of a type of room in which the hazard detector is installed. For instance, during an initial setup process or via an online account, a user may specify the type of room in which the hazard detector is installed. The user may select from choices such as: kitchen, hallway, bedroom, bathroom, basement, living room, dining room, study, library, poolroom, entertainment room, etc. in some embodiments, if the initial configuration is performed via a wireless device in communication with the hazard detector, the user may select from a list of available room types in order to specify which type of room the hazard detector will be (or has been) installed in.

At block 807, it may be determined whether the hazard detector has been or will be installed in a bedroom based upon the received indication at block 805. As a default setting or some other form of predefined assignment, the conditional lighting feature may be deactivated for bedrooms. For some or all other types of rooms, the conditional lighting feature may be, by default, activated. If, at block 807, it is determined that the user selected bedroom as the type of room in which the hazard detectors installed at block 805, the light may not be illuminated at block 808. Therefore, regardless of whether the ambient environment of the hazard detector is determined to be darkened and motion is present, the nightlight feature may not cause a light of the hazard detector to be illuminated. However, if at block 807 it is determined that the hazard detector is installed in a room type other than a bedroom based upon the received indication of block 805, method 800 may proceed to block 810. In the illustrated embodiment of method 800, the bedroom is the only room type that is by default set to have the nightlight feature disabled. It should be understood that, in other embodiments, different and/or multiple types may, by default, have the nightlight feature disabled. While such a feature may, by default, be disabled, it may be possible for user to enable the nightlight feature, such as via an online user account with which the hazard detector has been linked.

Step 809 may only be performed if the hazard detector uses batteries as its sole power source. If a structure's power source is available, the hazard detector may obtain power from the structure's wired power source to provide conditional lighting. If the hazard detector is connected with the structure's power source, but the structure's power source is unavailable, block 809 may be performed. If only batteries are available for the hazard detector's power source, block 809 may be performed to determine if the hazard detector's batteries have a sufficient charge to provide conditional lighting. At block 809, the battery charge level is determined and compared to a threshold value. If above the threshold value, a sufficient charge is present to continue using conditional lighting and method 800 may proceed to block 810. If below the threshold value, the batteries have been determined to have a low charge and conditional lighting is disabled at block 808, at least until new batteries are installed or the batteries are recharged.

Blocks 810, 820, and 830 may be performed similarly to blocks 710 through 730 of method 700. In the illustrated embodiment of method 800, block 807 is performed prior to blocks 810 through 830. It should be understood that in other embodiments, block 807 may be performed after motion data and brightness data is gathered from the ambient environment of the hazard detector. However, it may be beneficial to perform block 807 prior to such blocks in order to reduce the amount of monitoring of the ambient environment of the hazard detector which needs to be performed.

At block 850, stored illumination definitions may be accessed by the hazard detector. Such stored illumination definitions may be stored using a non-transitory processor readable medium of the processing system of the hazard detector. For instance, referring to FIG. 6, an exemplary relationship between colors, animations, and states of the hazard detector is presented in the form of a table, such information may be stored in various formats other than a table by a hazard detector. Such stored illumination definitions may be accessed to retrieve how a light of the hazard detector should be illuminated in response to the hazard detector not being installed in a bedroom, the brightness level in the ambient environment being less than the threshold brightness value, and motion being detected in the ambient environment. In some embodiments, accessing such stored illumination definitions will yield an indication that the light of the hazard detector should be faded on and faded off in the color used for the light should be white.

At block 860, the light of the hazard detector may be activated. Activation of the light may be contingent on motion being detected in the ambient environment of the hazard detector, the brightness level having been determined to be less than the threshold brightness value, and the assigned room type being determined to not be a bedroom. Further, the animation color used to illuminate the light may be contingent on accessing the stored illumination definitions of block 850 and retrieving indications of the proper color and animation to be used. As such, when illuminated, the light may serve as a nightlight when the room in which the hazard detector is installed is dark and motion has been detected. Because activation of the light is contingent on motion and a darkened environment, the nightlight feature is activated only when it is likely needed by a user. Following activation at block 860, method 800 may repeat (such as, from block 810) until either the ambient environment of the hazard detector is no longer darker than the threshold brightness value or motion is no longer detected in the ambient environment of the hazard detector. At this time, the light of the hazard detector may cease illuminating for uses the nightlight feature.

Figure 9:
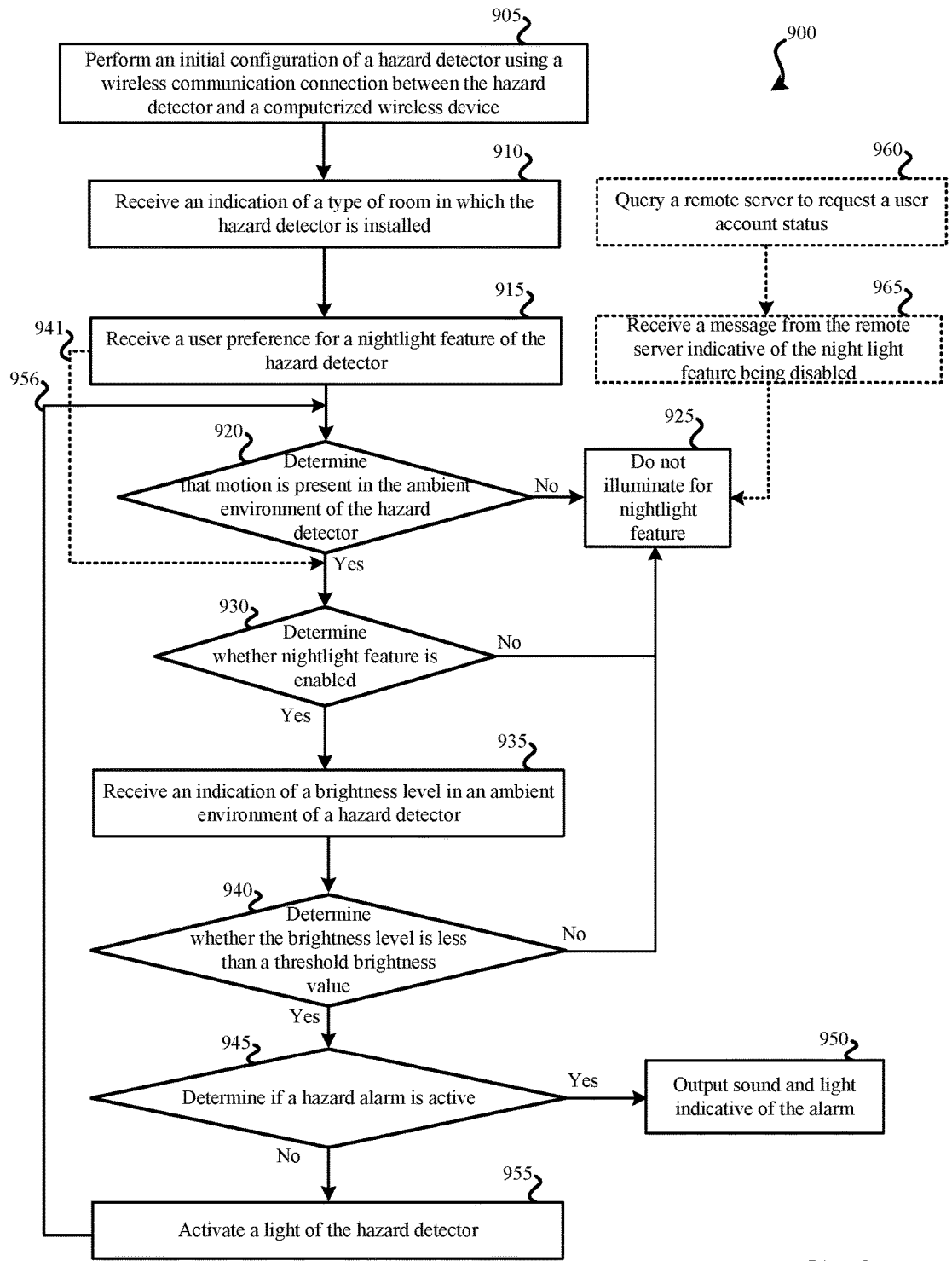
FIG. 9 illustrates an embodiment of a method for providing conditional lighting by a hazard detector contingent upon at least an initial configuration of the hazard detector and user preferences.

FIG. 9 illustrates an embodiment of a method 900 for providing conditional lighting by a hazard detector contingent upon at least an initial configuration of the hazard detector and user preferences. Method 900 may be performed using any of the embodiments of hazard detectors detailed in relation to FIGS. 1 through 5. Further, it may be possible that other embodiments of hazard detectors may be used to perform the blocks of method 900. Each block of method 900 may be understood as generally being performed by a hazard detector or a component of the hazard detector. Method 900 may represent a more detailed embodiment of method 700 of FIG. 7 and/or method 800 of FIG. 8. As such, any or all blocks performed as part of method 700 and/or method 800 may also be performed as part of method 900.

At block 905, initial configuration of the hazard detector may be performed. Such an initial configuration may be performed using a wireless communication connection between the hazard detector and the computerized wireless device. For instance, such a wireless communication connection may be directly between the hazard detector and the wireless device. In some embodiments, the hazard detector may create a wireless local area network connection for the computerized wireless device to join. In other embodiments, configuration of the hazard detector may occur from the wireless device via a wireless network operated by a router or other device that serves as an intermediary between the hazard detector in the computerized wireless device. In still other embodiments, it may be possible to connect a computerized device to the hazard detector via a wired connection. During such an initial configuration, block 910 may be performed. block 910 may be performed similarly to block 805 of method 800. Additionally, at block 915, either during the initial configuration or at a later time, such as by accessing settings associated with the hazard detector via an online user account, a user preference may be received that is indicative of whether the nightlight feature of the hazard detector should be enabled or disabled. As an example, if the type of room specified at block 910 is a kitchen, by default, the nightlight feature may be enabled. However, the user may specify via a user preference that the nightlight feature is to be disabled rather than enabled. As another example, if the type of room specified at block 910 is a bedroom, by default the nightlight feature may be disabled. However, the user may specify, via a user preference, that the nightlight feature is to be enabled rather than disabled.

At block 920, it may be determined whether motion is present in the ambient environment of the hazard detector. A motion sensor or, more generally, a presence sensor may collect infrared light from the environment of the hazard detector to assess whether it is likely that a user is present or not. If not, method 900 may proceed from block 920 to block 925. If motion is present, method 900 may proceed from block 920 to block 930. In some embodiments, the ambient environment is monitored for motion regardless of the nightlight feature being enabled or disabled. As such, even if the nightlight feature is disabled, the hazard detector may monitor for the user's presence. In some embodiments, the brightness level of the ambient environment of the hazard detector may not be monitored unless motion is determined to be present. As such, power may be saved by the hazard detector by not needing to monitor the brightness level of the ambient environment unless is likely that a user is in the ambient environment of the hazard detector.

In some embodiments, block 920 may not be involved in determining whether the nightlight feature should be enabled. For instance, the hazard detector may still be determining if motion is present, but may use such a determination for other features of the hazard detector. As illustrated by dotted line 941, whether motion is detected in the ambient environment of the hazard detector may not be relevant to whether the nightlight feature is enabled. In some embodiments, a user preference, which the user can set at the hazard detector via preferences maintained by a remote server, is used to define whether motion is used in determining whether the nightlight feature should be enabled. The ability to have the nightlight feature enabled regardless of motion may be restricted to only hazard detectors that use a wired, structure power supply. Hazard detectors that rely solely on battery power may not have such a preference available.

At block 930, a determination of whether the nightlight feature is enabled or disabled may be made. Such a determination may be contingent on the type of room indicated at block 910 and any user preference that may have been received at block 915. If no user preference was received at block 915, the default setting of whether the nightlight feature is enabled or disabled may be contingent on the type of room there was received in the indication of block 910. If the nightlight feature is disabled, method 900 may proceed to block 925. By default, the nightlight feature may be disabled for bedrooms but enabled for some or all other types of rooms. At block 925, the light of the hazard detector is not illuminated for use as the nightlight feature. It should be understood, however, that the light may be illuminated for other purposes, such as to signal a hazard being present, such as smoke or carbon monoxide.

If at block 930 it is determined that the nightlight feature is enabled, method 900 may proceed to block 935. blocks 935 and 940 may proceed similarly to blocks 710 and 730 of method 700. At block 935, indication of a brightness level in the ambient environment of the hazard detector may be received from a light sensor of the hazard detector by a processing system of the hazard detector. At block 940, it may be determined whether the brightness level in the ambient environment of the hazard detector is less than (and/or equal to) a threshold brightness value. If the brightness level is less than the threshold brightness value, method 900 may proceed to block 940. Otherwise, method 900 may proceed to block 925. If block 940 is not to be performed because method 900 proceeded to block 925, the motion detector of the hazard detector may be disabled in some embodiments. That is, in some embodiments, the motion detector may only be enabled in specific situations, such as when motion data is needed to determine whether the nightlight feature is to be activated. In other embodiments, the motion detector may remain enabled, such as for use in relation to other features of the hazard detector.

In some embodiments, as part of block 930 or separately, a check of a battery charge level of the hazard detector may be performed. If the hazard detector is being powered off of the battery, the hazard detector may disable the nightlight feature (and proceed to block 925) if the charge level of the battery is below a threshold value. If the hazard detector is actively being powered from a wired power supply of the structure (structure power source), the nightlight feature may be enabled regardless of the battery charge level. If disabled due to low charge level of the hazard detector's one or more batteries, the hazard detector may transmit a message to the remote server such that when the user accesses the remote server via a computerized device, the user is informed of the low battery level and, possibly, receives an indication of why the nightlight feature is disabled.

At block 945, it may be determined whether a hazard alarm is active. Whenever a hazard alarm is active during method 900, the nightlight feature may immediately be disabled such that the light may be used to alert the user to the presence of the hazard, such as by the light being illuminated a different color and/or using a different animation at block 950. For instance, if the nightlight feature involves the light of the hazard detector being illuminated using white light, if the hazard alarm is present, the light may be illuminated the color red and, possibly, a more urgent animation may be used for illuminating the light. It should be understood that block 945 may be performed at any point throughout method 900. For instance, if the hazard is ever detected by any hazard sensor onboard the hazard detector, method 900 may be interrupted and block 950 may be performed such that an auditory alarm indicative of the hazard and a light color and animation is output by the hazard detector's light that is also indicative of the alarm.

If no hazard alarm is active at block 945, method 900 may proceed to block 955. At block 955, the light of the hazard detector may be activated using the nightlight feature for at least a predefined period of time, such as five seconds. Activation of the light may be contingent on motion being detected in the ambient environment of the hazard detector, the brightness level having been determined to be less than the threshold brightness value, the nightlight feature being enabled, and no alarm sounding. Further, the animation color used to illuminate the light may be contingent on accessing stored illumination definitions and retrieving indication of the proper color and animation to be used as detailed in relation to block 850 of method 800. When illuminated, the light may serve as a nightlight when the room in which the hazard detector is installed is dark and motion has been detected. Because activation of the light is contingent on motion and a darkened environment, the nightlight feature is activated only when it is likely needed by a user. Following activation at block 955, method 900 may repeat such as, from block 920 (as indicated by arrow 956) or block 930, until either the ambient environment of the hazard detector is no longer darker than the threshold brightness value or motion is no longer detected in the ambient environment of the hazard detector. At which time, the light of the hazard detector may cease illuminating for the nightlight feature.

If arrow 956 has been performed once, such that the light has been activated, and a user's motion is no longer detected at block 920, a fade out animation of the light may occur to transition to block 925. This fade out animation may result in the light slowly being faded to off, such as over several seconds. If during this time period of the fade out animation motion of a user is again detected, the brightness of the light may be increased such that the light is again illuminated at a constant brightness level.

Further, method 900 may involve the hazard detector periodically querying a remote server to request a user account status at block 960. For instance, the hazard detector may query the remote server once per day. The user account status requested by the hazard detector may be of a user account linked with the hazard detector during the initial configuration performed at block 905. In response to this query, the hazard detector may receive one or more messages at block 965. If a user has updated a preference at the user account relevant to the hazard detector, one or more of the messages received at block 965 may be indicative of the updated preference. For instance, if the user specified to the remote server that the nightlight features is to be disabled, at block 965 the hazard detector may receive a message indicative of the nightlight feature being disabled. Additionally or alternatively, the user may specify a brightness level for the nightlight feature. For instance, the user may have the option of selecting between a predefined number of brightness levels, such as low, medium, and high, or may be permitted to use a graphical slider interface to select a customized brightness level. In some embodiments, regardless of when the user updates such a preference or option, the hazard detector may not be updated until the next time that the hazard detector queries the remote server. In some embodiments, the default brightness level may be set based on whether the hazard detector is connected to a structure's wired power supply or solely based on one or more batteries of the hazard detector. Also, additionally or alternatively, the user may be able to indicate that the nightlight feature should function independently of motion or a presence. As such, the light may illuminate based on the brightness level of the ambient environment of the hazard detector, but not based on whether motion or, more generally, a presence is detected.

The user can update his preferences at any time via a computerized device and the remote server; however, the preference may not take effect until the hazard detector queries and retrieves the updated preferences. In some embodiments, the user may be able to cause the hazard detector to query the remote server by providing user input, such as by actuating a button of the hazard detector. While the nightlight feature may not be illuminated at block 925 if disabled based on a user preference, the light of the hazard detector may still be used for outputting light in other instances, such as during a hazard or to provide an indication of status of the hazard detector. It is to be appreciated that while the described methods and systems for conditional pathway lighting are particularly advantageous in view of the particular device context, in that hazard detectors represent important life safety devices and are likely to be placed in many rooms around the house, and in that hazard detectors are likely to be well-positioned for viewing from many places in these rooms, and in that hazard detectors can be outfitted quite readily integrated sensors and lights as described herein, the scope of the present disclosure is not so limited. Rather, the described methods and systems for conditional pathway lighting are widely applicable to any of a variety of smart-home devices such as certain of those described in relation to FIG. 10 supra that may not historically have been purposed for such a function, including, but not limited to, environmental sensors, motion sensors, occupancy sensors, remote controllers, key fob remote controllers, smart-home hubs, microphones, speakers, door sensors, window sensors, generic programmable wireless control buttons, and home service robots. Although widely applicable for any of such smart-home devices, one or more of the described methods and systems become increasingly advantageous when applied in the context of devices that may be located in relatively readily-viewable locations and/or well-traveled locations in the home. According to one embodiment, the user can be provided with a suite of related smart-home devices, such as may be provided by a common manufacturer or group or badged to work with a common "ecosystem" of that manufacturer or group, wherein each of the devices, where practicable, provides a same or similar conditional pathway lighting feature according to a visually similar scheme and theme such as that described herein, such that the user can be readily familiar with the function provided without needing to become accustomed to a different scheme or theme for each device. Thus, by way of example, there can be provided a suite of devices including a security/automation hub, multiple door/window sensors, and multiple hazard detectors, wherein each such device has light and motion sensors and a circular illumination ring (of different physical scales as needed) and performs conditional pathway lighting according to the themes and schemes described herein. Having read this disclosure, one having skill in the art could apply the methods and systems of the present invention in the context of one or more of the above-described smart home devices.

Figure 10:
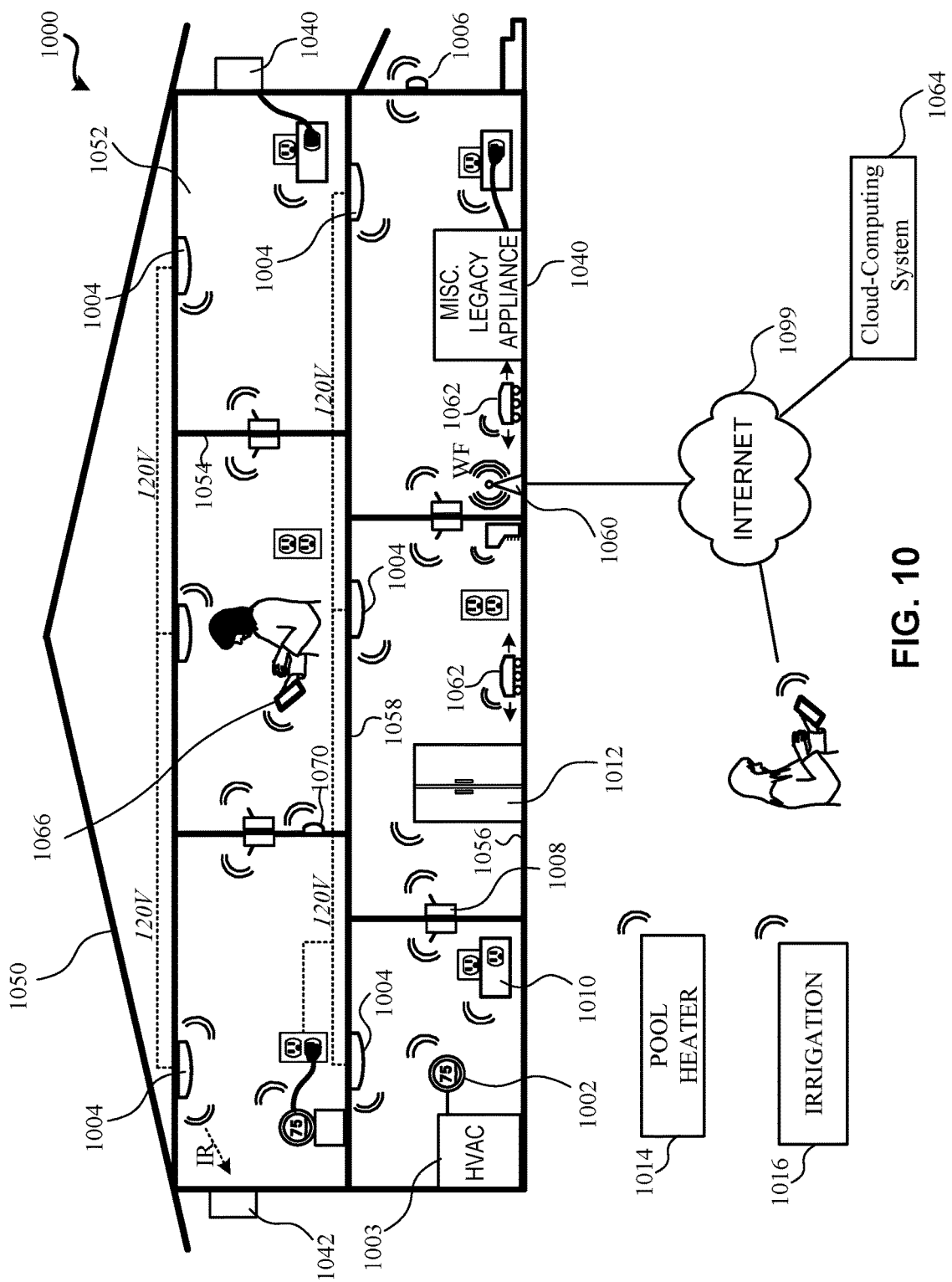
FIG. 10 illustrates an embodiment of a smart-home environment within which one or more of the devices, methods, systems, services, and/or computer program products described herein may be applicable.

Hazard detectors, as detailed herein, may be installed in a smart-home environment. FIG. 10 illustrates an example of a smart-home environment 1000 within which one or more of the devices, methods, systems, services, and/or computer program products described further herein can be applicable. The depicted smart-home environment 1000 includes a structure 1050, which can include, e.g., a house, office building, garage, or mobile home. It will be appreciated that devices can also be integrated into a smart-home environment 1000 that does not include an entire structure 1050, such as an apartment, condominium, or office space. Further, the smart home environment can control and/or be coupled to devices outside of the actual structure 1050. Indeed, several devices in the smart home environment need not physically be within the structure 1050 at all. For example, a device controlling a pool heater or irrigation system can be located outside of the structure 1050.

The depicted structure 1050 includes a plurality of rooms 1052, separated at least partly from each other via walls 1054. The walls 1054 can include interior walls or exterior walls. Each room can further include a floor 1056 and a ceiling 1058. Devices can be mounted on, integrated with and/or supported by a wall 1054, floor 1056 or ceiling 1058.

In some embodiments, the smart-home environment 1000 of FIG. 10 includes a plurality of devices, including intelligent, multi-sensing, network-connected devices, that can integrate seamlessly with each other and/or with a central server or a cloud-computing system to provide any of a variety of useful smart-home objectives. The smart-home environment 1000 may include one or more intelligent, multi-sensing, network-connected thermostats 1002 (hereinafter referred to as smart thermostats 1002), one or more intelligent, network-connected, hazard detectors 1004, and one or more intelligent, multi-sensing, network-connected entryway interface devices 1006 (hereinafter referred to as "smart doorbells 1006"). According to embodiments, the smart thermostat 1002 detects ambient climate characteristics (e.g., temperature and/or humidity) and controls a HVAC system 1003 accordingly. The hazard detector 1004 may detect the presence of a hazardous substance or a substance indicative of a hazardous substance (e.g., smoke, fire, or carbon monoxide). The smart doorbell 1006 may detect a person's approach to or departure from a location (e.g., an outer door), control doorbell functionality, announce a person's approach or departure via audio or visual means, or control settings on a security system (e.g., to activate or deactivate the security system when occupants go and come).

In some embodiments, the smart-home environment 1000 of FIG. 10 further includes one or more intelligent, multi-sensing, network-connected wall switches 1008 (hereinafter referred to as "smart wall switches 1008"), along with one or more intelligent, multi-sensing, network-connected wall plug interfaces 1010 (hereinafter referred to as "smart wall plugs 1010"). The smart wall switches 1008 may detect ambient lighting conditions, detect room-occupancy states, and control a power and/or dim state of one or more lights. In some instances, smart wall switches 1008 may also control a power state or speed of a fan, such as a ceiling fan. The smart wall plugs 1010 may detect occupancy of a room or enclosure and control supply of power to one or more wall plugs (e.g., such that power is not supplied to the plug if nobody is at home).

Still further, in some embodiments, the smart-home environment 1000 of FIG. 10 includes a plurality of intelligent, multi-sensing, network-connected appliances 1012 (hereinafter referred to as "smart appliances 1012"), such as refrigerators, stoves and/or ovens, televisions, washers, dryers, lights, stereos, intercom systems, garage-door openers, floor fans, ceiling fans, wall air conditioners, pool heaters, irrigation systems, security systems, and so forth. According to embodiments, the network-connected appliances 1012 are made compatible with the smart-home environment by cooperating with the respective manufacturers of the appliances. For example, the appliances can be space heaters, window AC units, motorized duct vents, etc. When plugged in, an appliance can announce itself to the smart-home network, such as by indicating what type of appliance it is, and it can automatically integrate with the controls of the smart-home. Such communication by the appliance to the smart home can be facilitated by any wired or wireless communication protocols known by those having ordinary skill in the art. The smart home also can include a variety of non-communicating legacy appliances 1040, such as old conventional washer/dryers, refrigerators, and the like which can be controlled, albeit coarsely (ON/OFF), by virtue of the smart wall plugs 1010. The smart-home environment 1000 can further include a variety of partially communicating legacy appliances 1042, such as infrared ("IR") controlled wall air conditioners or other IR-controlled devices, which can be controlled by IR signals provided by the hazard detectors 1004 or the smart wall switches 1008.

According to embodiments, the smart thermostats 1002, the hazard detectors 1004, the smart doorbells 1006, the smart wall switches 1008, the smart wall plugs 1010, and other devices of the smart-home environment 1000 are modular and can be incorporated into older and new houses. For example, the devices are designed around a modular platform consisting of two basic components: a head unit and a back plate, which is also referred to as a docking station. Multiple configurations of the docking station are provided so as to be compatible with any home, such as older and newer homes. However, all of the docking stations include a standard head-connection arrangement, such that any head unit can be removably attached to any docking station. Thus, in some embodiments, the docking stations are interfaces that serve as physical connections to the structure and the voltage wiring of the homes, and the interchangeable head units contain all of the sensors, processors, user interfaces, the batteries, and other functional components of the devices.

The smart-home environment 1000 may also include communication with devices outside of the physical home but within a proximate geographical range of the home. For example, the smart-home environment 1000 may include a pool heater monitor 1014 that communicates a current pool temperature to other devices within the smart-home environment 1000 or receives commands for controlling the pool temperature. Similarly, the smart-home environment 1000 may include an irrigation monitor 1016 that communicates information regarding irrigation systems within the smart-home environment 1000 and/or receives control information for controlling such irrigation systems. According to embodiments, an algorithm is provided for considering the geographic location of the smart-home environment 1000, such as based on the zip code or geographic coordinates of the home. The geographic information is then used to obtain data helpful for determining optimal times for watering; such data may include sun location information, temperature, due point, soil type of the land on which the home is located, etc.

By virtue of network connectivity, one or more of the smart-home devices of FIG. 10 can further allow a user to interact with the device even if the user is not proximate to the device. For example, a user can communicate with a device using a computer (e.g., a desktop computer, laptop computer, or tablet) or other portable electronic device (e.g., a smartphone) 1066. A webpage or app can be configured to receive communications from the user and control the device based on the communications and/or to present information about the device's operation to the user. For example, the user can view a current setpoint temperature for a device and adjust it, using a computer. The user can be in the structure during this remote communication or outside the structure.

As discussed, users can control and interact with the smart thermostat, hazard detectors 1004, and other smart devices in the smart-home environment 1000 using a network-connected computer or portable electronic device 1066. In some examples, some or all of the occupants (e.g., individuals who live in the home) can register their device 1066 with the smart-home environment 1000. Such registration can be made at a central server to authenticate the occupant and/or the device as being associated with the home and to give permission to the occupant to use the device to control the smart devices in the home. An occupant can use his registered device 1066 to remotely control the smart devices of the home, such as when the occupant is at work or on vacation. The occupant may also use his registered device to control the smart devices when the occupant is actually located inside the home, such as when the occupant is sitting on a couch inside the home. It should be appreciated that, instead of or in addition to registering devices 1066, the smart-home environment 1000 makes inferences about which individuals live in the home and are therefore occupants and which devices 1066 are associated with those individuals. As such, the smart-home environment "learns" who is an occupant and permits the devices 1066 associated with those individuals to control the smart devices of the home.

In some embodiments, in addition to containing processing and sensing capabilities, each of the devices 1002, 1004, 1006, 1008, 1010, 1012, 1014, and 1016 (collectively referred to as "the smart devices") is capable of data communications and information sharing with any other of the smart devices, as well as to any central server or cloud-computing system or any other device that is network-connected anywhere in the world. The required data communications can be carried out using any of a variety of custom or standard wireless protocols (Wi-Fi, ZigBee, 6LoWPAN, etc.) and/or any of a variety of custom or standard wired protocols (CAT6 Ethernet, HomePlug, etc.)

According to embodiments, all or some of the smart devices can serve as wireless or wired repeaters. For example, a first one of the smart devices can communicate with a second one of the smart devices via a wireless router 1060. The smart devices can further communicate with each other via a connection to a network, such as the Internet 1099. Through the Internet 1099, the smart devices can communicate with a cloud-computing system 1064, which can include one or more centralized or distributed server systems. The cloud-computing system 1064 can be associated with a manufacturer, support entity, or service provider associated with the device. For one embodiment, a user may be able to contact customer support using a device itself rather than needing to use other communication means such as a telephone or Internet-connected computer. Further, software updates can be automatically sent from cloud-computing system 1064 to devices (e.g., when available, when purchased, or at routine intervals).

According to embodiments, the smart devices combine to create a mesh network of spokesman and low-power nodes in the smart-home environment 1000, where some of the smart devices are "spokesman" nodes and others are "low-powered" nodes. Some of the smart devices in the smart-home environment 1000 are battery powered, while others have a regular and reliable power source, such as by connecting to wiring (e.g., to 120V line voltage wires) behind the walls 1054 of the smart-home environment. The smart devices that have a regular and reliable power source are referred to as "spokesman" nodes. These nodes are equipped with the capability of using any wireless protocol or manner to facilitate bidirectional communication with any of a variety of other devices in the smart-home environment 1000 as well as with the cloud-computing system 1064. On the other hand, the devices that are battery powered are referred to as "low-power" nodes. These nodes tend to be smaller than spokesman nodes and can only communicate using wireless protocols that require very little power, such as Zigbee, 6LoWPAN, etc. Further, some, but not all, low-power nodes are incapable of bidirectional communication. These low-power nodes send messages, but they are unable to "listen". Thus, other devices in the smart-home environment 1000, such as the spokesman nodes, cannot send information to these low-power nodes.

As described, the smart devices serve as low-power and spokesman nodes to create a mesh network in the smart-home environment 1000. Individual low-power nodes in the smart-home environment regularly send out messages regarding what they are sensing, and the other low-powered nodes in the smart-home environment—in addition to sending out their own messages—repeat the messages, thereby causing the messages to travel from node to node (i.e., device to device) throughout the smart-home environment 1000. The spokesman nodes in the smart-home environment 1000 are able to "drop down" to low-powered communication protocols to receive these messages, translate the messages to other communication protocols, and send the translated messages to other spokesman nodes and/or cloud-computing system 1064. Thus, the low-powered nodes using low-power communication protocols are able to send messages across the entire smart-home environment 1000 as well as over the Internet 1099 to cloud-computing system 1064. According to embodiments, the mesh network enables cloud-computing system 1064 to regularly receive data from all of the smart devices in the home, make inferences based on the data, and send commands back to one of the smart devices to accomplish some of the smart-home objectives described herein.

As described, the spokesman nodes and some of the low-powered nodes are capable of "listening." Accordingly, users, other devices, and cloud-computing system 1064 can communicate controls to the low-powered nodes. For example, a user can use the portable electronic device (e.g., a smartphone) 1066 to send commands over the Internet 1099 to cloud-computing system 1064, which then relays the commands to the spokesman nodes in the smart-home environment 1000. The spokesman nodes drop down to a low-power protocol to communicate the commands to the low-power nodes throughout the smart-home environment, as well as to other spokesman nodes that did not receive the commands directly from the cloud-computing system 1064.

An example of a low-power node is a smart nightlight 1070. In addition to housing a light source, the smart nightlight 1070 houses an occupancy sensor, such as an ultrasonic or passive IR sensor, and an ambient light sensor, such as a photoresistor or a single-pixel sensor that measures light in the room. In some embodiments, the smart nightlight 1070 is configured to activate the light source when its ambient light sensor detects that the room is dark and when its occupancy sensor detects that someone is in the room. In other embodiments, the smart nightlight 1070 is simply configured to activate the light source when its ambient light sensor detects that the room is dark. Further, according to embodiments, the smart nightlight 1070 includes a low-power wireless communication chip (e.g., ZigBee chip) that regularly sends out messages regarding the occupancy of the room and the amount of light in the room, including instantaneous messages coincident with the occupancy sensor detecting the presence of a person in the room. As mentioned above, these messages may be sent wirelessly, using the mesh network, from node to node (i.e., smart device to smart device) within the smart-home environment 1000 as well as over the Internet 1099 to cloud-computing system 1064.

Other examples of low-powered nodes include battery-operated versions of the hazard detectors 1004. These hazard detectors 1004 are often located in an area without access to constant and reliable (e.g., structural) power and, as discussed in detail below, may include any number and type of sensors, such as smoke/fire/heat sensors, carbon monoxide/dioxide sensors, occupancy/motion sensors, ambient light sensors, temperature sensors, humidity sensors, and the like. Furthermore, hazard detectors 1004 can send messages that correspond to each of the respective sensors to the other devices and cloud-computing system 1064, such as by using the mesh network as described above.

Examples of spokesman nodes include smart doorbells 1006, smart thermostats 1002, smart wall switches 1008, and smart wall plugs 1010. These devices 1002, 1006, 1008, and 1010 are often located near and connected to a reliable power source, and therefore can include more power-consuming components, such as one or more communication chips capable of bidirectional communication in any variety of protocols.

In some embodiments, the mesh network of low-powered and spokesman nodes can be used to provide exit lighting in the event of an emergency. In some instances, to facilitate this, users provide pre-configuration information that indicates exit routes in the smart-home environment 1000. For example, for each room in the house, the user provides a map of the best exit route. It should be appreciated that instead of a user providing this information, cloud-computing system 1064 or some other device could automatically determine the routes using uploaded maps, diagrams, architectural drawings of the smart-home house, as well as using a map generated based on positional information obtained from the nodes of the mesh network (e.g., positional information from the devices is used to construct a map of the house). In operation, when an alarm is activated (e.g., when one or more of the hazard detectors 1004 detect smoke and activates an alarm), cloud-computing system 1064 or some other device uses occupancy information obtained from the low-powered and spokesman nodes to determine which rooms are occupied and then turns on lights (e.g., smart nightlights 1070, wall switches 1008, smart wall plugs 1010 that power lamps, etc.) along the exit routes from the occupied rooms so as to provide emergency exit lighting.

Further included and illustrated in the exemplary smart-home environment 1000 of FIG. 10 are service robots 1062, each configured to carry out, in an autonomous manner, any of a variety of household tasks. For some embodiments, the service robots 1062 can be respectively configured to perform floor sweeping, floor washing, etc. in a manner similar to that of known commercially available devices such as the Roomba™ and Scooba™ products sold by iRobot, Inc. of Bedford, Mass. Tasks such as floor sweeping and floor washing can be considered as "away" or "while-away" tasks for purposes of the instant description, as it is generally more desirable for these tasks to be performed when the occupants are not present. For other embodiments, one or more of the service robots 1062 are configured to perform tasks such as playing music for an occupant, serving as a localized thermostat for an occupant, serving as a localized air monitor/purifier for an occupant, serving as a localized baby monitor, serving as a localized hazard detector for an occupant, and so forth, it being generally more desirable for such tasks to be carried out in the immediate presence of the human occupant. For purposes of the instant description, such tasks can be considered as "human-facing" or "human-centric" tasks.

When serving as a localized air monitor/purifier for an occupant, a particular service robot 1062 can be considered to be facilitating what can be called a "personal health-area network" for the occupant, with the objective being to keep the air quality in the occupant's immediate space at healthy levels. Alternatively or in conjunction therewith, other health-related functions can be provided, such as monitoring the temperature or heart rate of the occupant (e.g., using finely remote sensors, near-field communication with on-person monitors, etc.). When serving as a localized hazard detector for an occupant, a particular service robot 1062 can be considered to be facilitating what can be called a "personal safety-area network" for the occupant, with the objective being to ensure there is no excessive carbon monoxide, smoke, fire, etc., in the immediate space of the occupant. Methods analogous to those described above for personal comfort-area networks in terms of occupant identifying and tracking are likewise applicable for personal health-area network and personal safety-area network embodiments.

According to some embodiments, the above-referenced facilitation of personal comfort-area networks, personal health-area networks, personal safety-area networks, and/or other such human-facing functionalities of the service robots 1062, are further enhanced by logical integration with other smart sensors in the home according to rules-based inferencing techniques or artificial intelligence techniques for achieving better performance of those human-facing functionalities and/or for achieving those goals in energy-conserving or other resource-conserving ways. Thus, for one embodiment relating to personal health-area networks, the air monitor/purifier service robot 1062 can be configured to detect whether a household pet is moving toward the currently settled location of the occupant (e.g., using on-board sensors and/or by data communications with other smart-home sensors along with rules-based inferencing/artificial intelligence techniques), and if so, the air purifying rate is immediately increased in preparation for the arrival of more airborne pet dander. For another embodiment relating to personal safety-area networks, the hazard detector service robot 1062 can be advised by other smart-home sensors that the temperature and humidity levels are rising in the kitchen, which is nearby the occupant's current dining room location, and responsive to this advisory, the hazard detector service robot 1062 will temporarily raise a hazard detection threshold, such as a smoke detection threshold, under an inference that any small increases in ambient smoke levels will most likely be due to cooking activity and not due to a genuinely hazardous condition.

Figure 11:
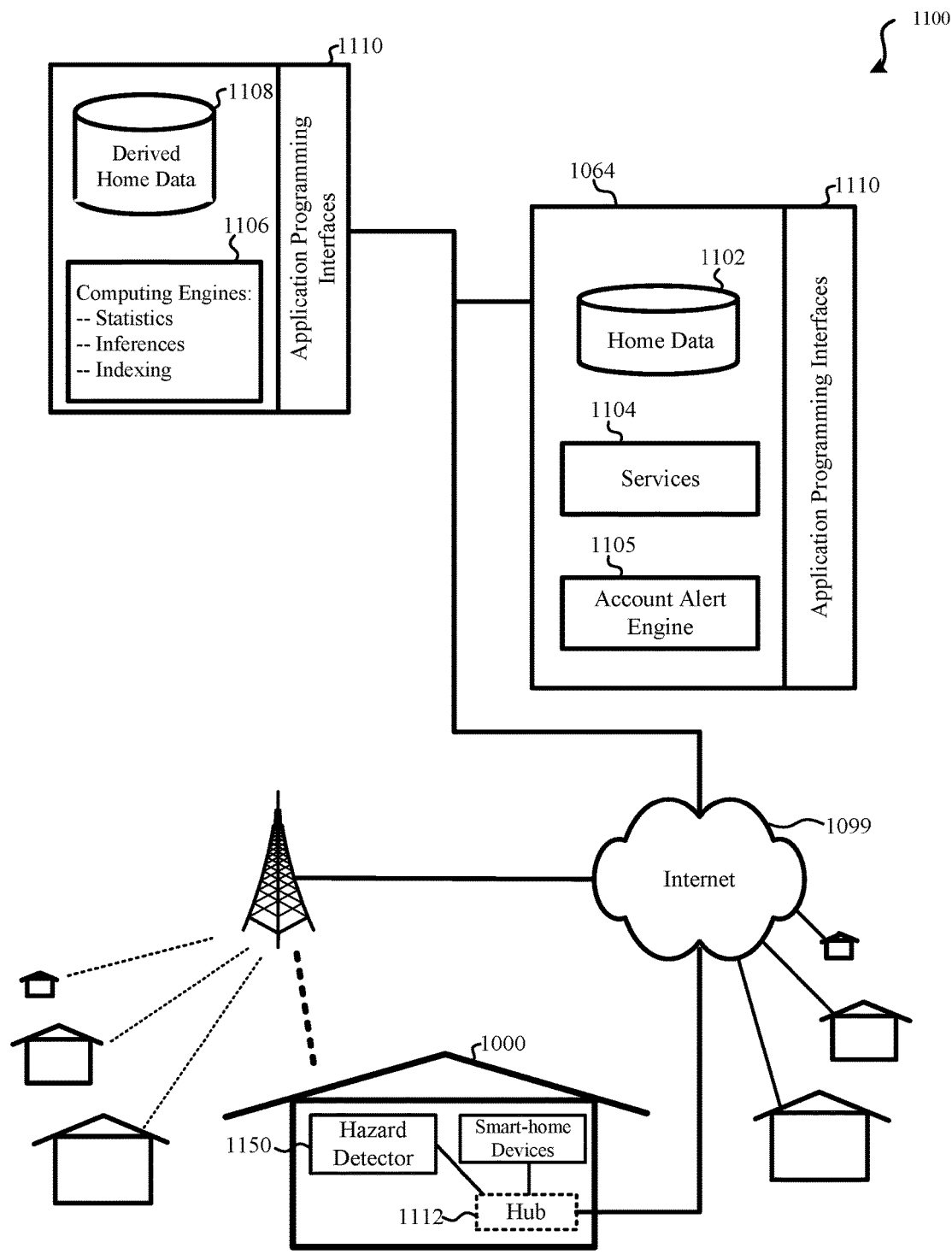
FIG. 11 illustrates a network-level view of the extensible devices and services platform with which a hazard detector may be integrated.

FIG. 11 illustrates a network-level view of an extensible devices and services platform 1100 with which a plurality of smart-home environments, such as the smart-home environment 1000 of FIG. 10, can be integrated. The extensible devices and services platform 1100 includes cloud-computing system 1064. Each of the intelligent, network-connected devices 1002, 1004, 1006, 1008, 1010, 1012, 1014, and 1016 from FIG. 10 may communicate with cloud-computing system 1064. For example, a connection to the Internet 1099 can be established either directly (for example, using 3G/4G connectivity to a wireless carrier), through a hubbed network 1112 (which can be a scheme ranging from a simple wireless router, for example, up to and including an intelligent, dedicated whole-home control node), or through any combination thereof.

Although in some examples provided herein, the devices and services platform 1100 communicates with and collects data from the smart devices of smart-home environment 1000 of FIG. 10, it should be appreciated that the devices and services platform 1100 communicates with and collects data from a plurality of smart-home environments across the world. For example, cloud-computing system 1064 can collect home data 1102 from the devices of one or more smart-home environments, where the devices can routinely transmit home data or can transmit home data in specific instances (e.g., when a device queries the home data 1102). Thus, the devices and services platform 1100 routinely collects data from homes across the world. As described, the collected home data 1102 includes, for example, power consumption data, occupancy data, HVAC settings and usage data, carbon monoxide levels data, carbon dioxide levels data, volatile organic compounds levels data, sleeping schedule data, cooking schedule data, inside and outside temperature humidity data, television viewership data, inside and outside noise level data, etc.

Cloud-computing system 1064 can further provide one or more services 1104. The services 1104 can include, e.g., software updates, customer support, sensor data collection/logging, remote access, remote or distributed control, or use suggestions (e.g., based on collected home data 1102 to improve performance, reduce utility cost, etc.). Data associated with the services 1104 can be stored at cloud-computing system 1064 and cloud-computing system 1064 can retrieve and transmit the data at an appropriate time (e.g., at regular intervals, upon receiving a request from a user, etc.).

As part of services 1104, user accounts may be maintained by the cloud-computing system 1064. The user account may store subscription information, billing information, registration information, user preferences, and/or other data associated with various smart-home devices, such as one or more hazard detectors, installed within a structure that is linked with a user account. Occasionally, attention of a user to his or her user account may be requested. In response to a query from hazard detector 1150 (or other smart-home device), a message may be transmitted by the cloud-computing system 1064 to hazard detector 1150 (which may represent any of the previously described hazard detectors) indicating that a status output by hazard detector 1150 should indicate that a user is requested to log in to his or her user account. Further detail regarding the requested log may be transmitted by service 1104 to hazard detector 1150. For instance, the reason for the requested login may be expired payment information (such as an expired credit card). The user can request detail on a status output by hazard detector 1150, which may be presented to the user as a color and animation output via a light of hazard detector 1150. The request for detail may be by performing a gesture within the vicinity of hazard detector 1150. A spoken message may then be output by hazard detector 1150, indicating that the user is requested to log in to his account and may also indicate the reason of the payment information needing to be updated. As such, a status check performed by hazard detector 1150 may not only check the status of hazard detector 1150 itself, but also the state of a remotely-maintained user account.

As illustrated in FIG. 11, an embodiment of the extensible devices and services platform 1100 includes a processing engine 1106, which can be concentrated at a single server or distributed among several different computing entities without limitation. The processing engine 1106 can include computerized engines (e.g., software executed by hardware) configured to receive data from devices of smart-home environments (e.g., via the Internet or a hubbed network), to index the data, to analyze the data and/or to generate statistics based on the analysis or as part of the analysis. The analyzed data can be stored as derived home data 1108.

Results of the analysis or statistics can thereafter be transmitted back to the device that provided home data used to derive the results, to other devices, to a server providing a webpage to a user of the device, or to other non-device entities. For example, use statistics, use statistics relative to use of other devices, use patterns, and/or statistics summarizing sensor readings can be generated by the processing engine 1106 and transmitted. The results or statistics can be provided via the Internet 1099. In this manner, the processing engine 1106 can be configured and programmed to derive a variety of useful information from the home data 1102. A single server can include one or more engines.

In some embodiments, to encourage innovation and research and to increase products and services available to users, the devices and services platform 1100 exposes a range of application programming interfaces (APIs) 1110 to third parties, such as charities, governmental entities (e.g., the Food and Drug Administration or the Environmental Protection Agency), academic institutions (e.g., university researchers), businesses (e.g., providing device warranties or service to related equipment, targeting advertisements based on home data), utility companies, and other third parties. The APIs 1110 may be coupled to and permit third-party systems to communicate with cloud-computing system 1064, including the services 1104, the processing engine 1106, the home data 1102, and the derived home data 1108. For example, the APIs 1110 allow applications executed by the third parties to initiate specific data processing tasks that are executed by cloud-computing system 1064, as well as to receive dynamic updates to the home data 1102 and the derived home data 1108.

Account alert engine may serve to determine whether a hazard detector should provide an indication that the user's account requires attention. For instance, account alert engine 1105 may periodically assess the state of a user's account, such as whether settings need updating, whether payment information is up-to-date, whether one or more messages are pending, whether payment is due, etc. If user attention is required, upon a request being received from a hazard detector and a look-up of the user's account being performed, account alert engine may respond with an indication that the user account requires attention. Additional detail may also be provided such that if the user performs a gesture or otherwise requests additional detail, such detail can be provided, such as via an auditory message. If user attention is not required, upon a request being received from a hazard detector and a look-up of the user's account being performed (e.g., by determining an account associated with the hazard detector from which the request was received), account alert engine may respond with an indication that the user account does not require attention.

FIG. 1200 illustrates an abstracted functional view of the extensible devices and services platform 1100 of FIG. 11, with particular reference to the processing engine 1106 as well as devices, such as those of the smart-home environment 1000 of FIG. 10. Even though devices situated in smart-home environments will have an endless variety of different individual capabilities and limitations, they can all be thought of as sharing common characteristics in that each of them is a data consumer 1265 (DC), a data source 1266 (DS), a services consumer 1267 (SC), and a services source 1268 (SS). Advantageously, in addition to providing the essential control information needed for the devices to achieve their local and immediate objectives, the extensible devices and services platform 1100 can also be configured to harness the large amount of data that is flowing out of these devices. In addition to enhancing or optimizing the actual operation of the devices themselves with respect to their immediate functions, the extensible devices and services platform 1100 can be directed to "repurposing" that data in a variety of automated, extensible, flexible, and/or scalable ways to achieve a variety of useful objectives. These objectives may be predefined or adaptively identified based on, e.g., usage patterns, device efficiency, and/or user input (e.g., requesting specific functionality).

Figure 12:
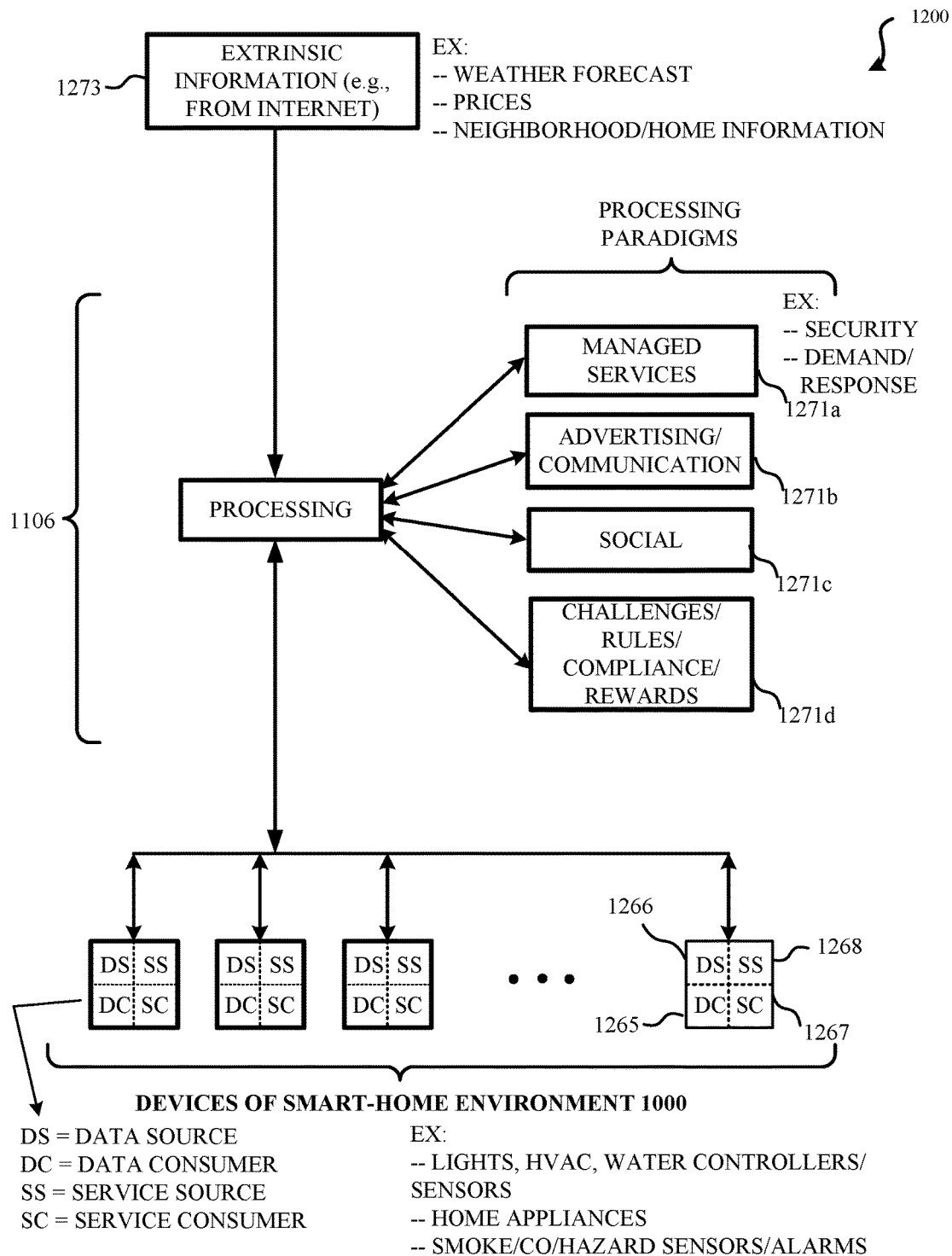
FIG. 12 illustrates an embodiment of an abstracted functional view of the extensible devices and services platform of FIG. 11, with reference to a processing engine as well as devices of the smart-home environment.

For example, FIG. 12 shows processing engine 1106 as including a number of paradigms 1271. Processing engine 1106 can include a managed services paradigm 1271*a* that monitors and manages primary or secondary device functions. The device functions can include ensuring proper operation of a device given user inputs, estimating that (e.g., and responding to an instance in which) an intruder is or is attempting to be in a dwelling, detecting a failure of equipment coupled to the device (e.g., a light bulb having burned out), implementing or otherwise responding to energy demand response events, or alerting a user of a current or predicted future event or characteristic. Processing engine 1106 can further include an advertising/communication paradigm 1271*b* that estimates characteristics (e.g., demographic information), desires and/or products of interest of a user based on device usage. Services, promotions, products or upgrades can then be offered or automatically provided to the user. Processing engine 1106 can further include a social paradigm 1271*c* that uses information from a social network, provides information to a social network (for example, based on device usage), and/or processes data associated with user and/or device interactions with the social network platform. For example, a user's status as reported to his trusted contacts on the social network could be updated to indicate when he is home based on light detection, security system inactivation or device usage detectors. As another example, a user may be able to share device-usage statistics with other users. In yet another example, a user may share HVAC settings that result in low power bills and other users may download the HVAC settings to their smart thermostat 1002 to reduce their power bills.

The processing engine 1106 can include a challenges/rules/compliance/rewards paradigm 1271*d* that informs a user of challenges, competitions, rules, compliance regulations and/or rewards and/or that uses operation data to determine whether a challenge has been met, a rule or regulation has been complied with and/or a reward has been earned. The challenges, rules or regulations can relate to efforts to conserve energy, to live safely (e.g., reducing exposure to toxins or carcinogens), to conserve money and/or equipment life, to improve health, etc. For example, one challenge may involve participants turning down their thermostat by one degree for one week. Those that successfully complete the challenge are rewarded, such as by coupons, virtual currency, status, etc. Regarding compliance, an example involves a rental-property owner making a rule that no renters are permitted to access certain owner's rooms. The devices in the room having occupancy sensors could send updates to the owner when the room is accessed.

The processing engine 1106 can integrate or otherwise utilize extrinsic information 1273 from extrinsic sources to improve the functioning of one or more processing paradigms. Extrinsic information 1273 can be used to interpret data received from a device, to determine a characteristic of the environment near the device (e.g., outside a structure that the device is enclosed in), to determine services or products available to the user, to identify a social network or social-network information, to determine contact information of entities (e.g., public-service entities such as an emergency-response team, the police or a hospital) near the device, etc., to identify statistical or environmental conditions, trends or other information associated with a home or neighborhood, and so forth.

An extraordinary range and variety of benefits can be brought about by, and fit within the scope of, the described extensible devices and services platform 1100, ranging from the ordinary to the profound. Thus, in one "ordinary" example, each bedroom of the smart-home environment 1000 can be provided with a smart wall switch 1008, a smart wall plug 1010, and/or smart hazard detectors 1004, all or some of which include an occupancy sensor, wherein the occupancy sensor is also capable of inferring (e.g., by virtue of motion detection, facial recognition, audible sound patterns, etc.) whether the occupant is asleep or awake. If a serious fire event is sensed, the remote security/monitoring service or fire department is advised of how many occupants there are in each bedroom, and whether those occupants are still asleep (or immobile) or whether they have properly evacuated the bedroom. While this is, of course, a very advantageous capability accommodated by the described extensible devices and services platform, there can be substantially more "profound" examples that can truly illustrate the potential of a larger "intelligence" that can be made available. By way of perhaps a more "profound" example, the same bedroom occupancy data that is being used for fire safety can also be "repurposed" by the processing engine 1106 in the context of a social paradigm of neighborhood child development and education. Thus, for example, the same bedroom occupancy and motion data discussed in the "ordinary" example can be collected and made available (properly anonymized) for processing in which the sleep patterns of schoolchildren in a particular ZIP code can be identified and tracked. Localized variations in the sleeping patterns of the schoolchildren may be identified and correlated, for example, to different nutrition programs in local schools.

Figure 13:
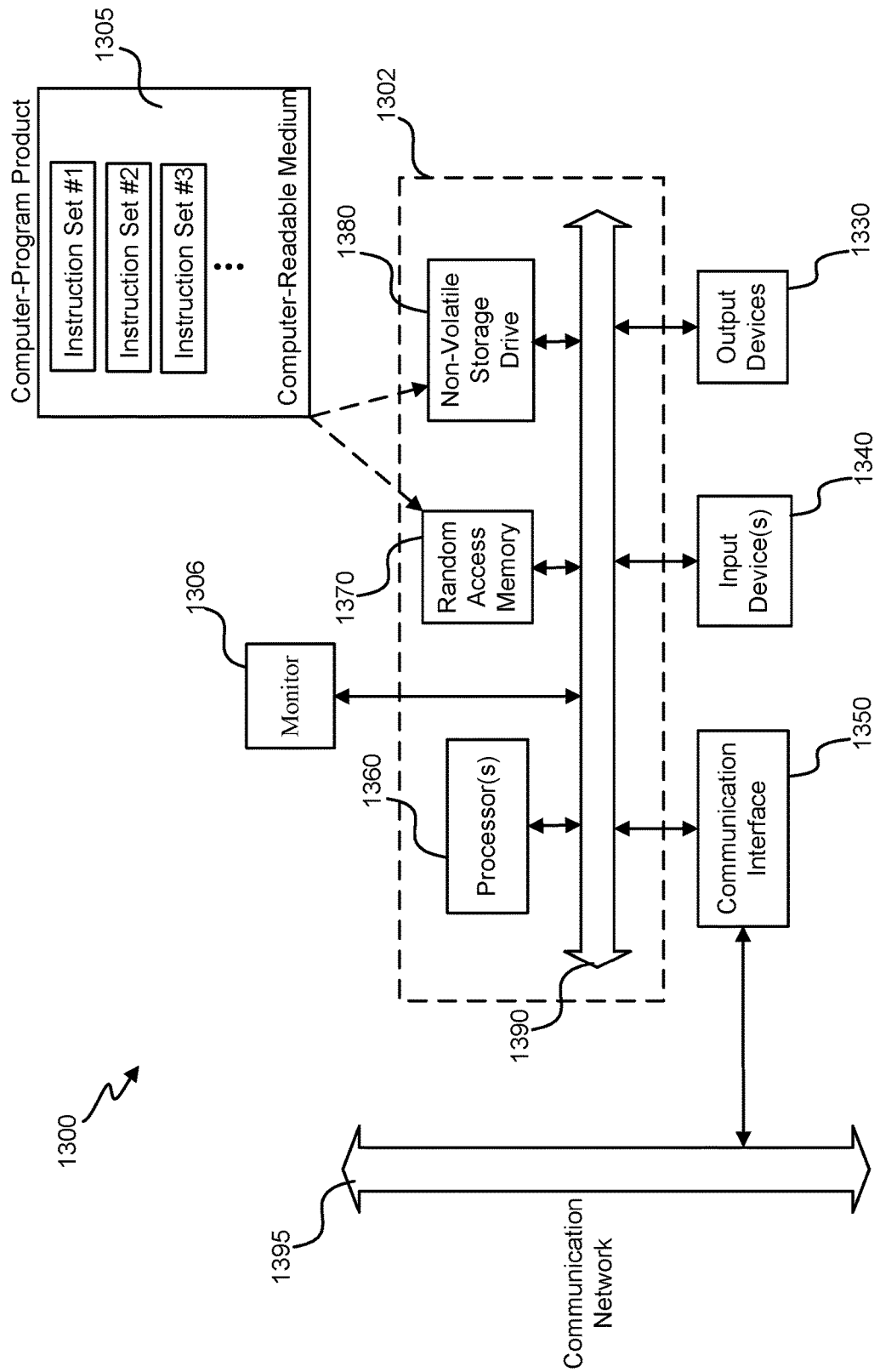
FIG. 13 illustrates an embodiment of a computer system.

With reference to FIG. 13, an embodiment of a special-purpose computer system 1300 is shown. For example, one or more intelligent components, processing system 110 and components thereof may be a special-purpose computer system 1300. Such a special-purpose computer system 1300 may be incorporated as part of a hazard detector and/or any of the other computerized devices discussed herein, such as a remote server, smart thermostat, or network. The above methods may be implemented by computer-program products that direct a computer system to perform the actions of the above-described methods and components. Each such computer-program product may comprise sets of instructions (codes) embodied on a computer-readable medium that direct the processor of a computer system to perform corresponding actions. The instructions may be configured to run in sequential order, or in parallel (such as under different processing threads), or in a combination thereof. After loading the computer-program products on a general purpose computer system 1326, it is transformed into the special-purpose computer system 1300.

Special-purpose computer system 1300 comprises a computer 1302, a monitor 1306 coupled to computer 1302, one or more additional user output devices 1330 (optional) coupled to computer 1302, one or more user input devices 1340 (e.g., keyboard, mouse, track ball, touch screen) coupled to computer 1302, an optional communications interface 1350 coupled to computer 1302, a computer-program product 1305 stored in a tangible computer-readable memory in computer 1302. Computer-program product 1305 directs computer system 1300 to perform the above-described methods. Computer 1302 may include one or more processors 1360 that communicate with a number of peripheral devices via a bus subsystem 1390. These peripheral devices may include user output device(s) 1330, user input device(s) 1340, communications interface 1350, and a storage subsystem, such as random access memory (RAM) 1370 and non-volatile storage drive 1380 (e.g., disk drive, optical drive, solid state drive), which are forms of tangible computer-readable memory.

Computer-program product 1305 may be stored in non-volatile storage drive 1380 or another computer-readable medium accessible to computer 1302 and loaded into random access memory (RAM) 1370. Each processor 1360 may comprise a microprocessor, such as a microprocessor from Intel® or Advanced Micro Devices, Inc.®, or the like. To support computer-program product 1305, the computer 1302 runs an operating system that handles the communications of computer-program product 1305 with the above-noted components, as well as the communications between the above-noted components in support of the computer-program product 1305. Exemplary operating systems include Windows® or the like from Microsoft Corporation, Solaris® from Sun Microsystems, LINUX, UNIX, and the like.

User input devices 1340 include all possible types of devices and mechanisms to input information to computer 1302. These may include a keyboard, a keypad, a mouse, a scanner, a digital drawing pad, a touch screen incorporated into the display, audio input devices such as voice recognition systems, microphones, and other types of input devices. In various embodiments, user input devices 1340 are typically embodied as a computer mouse, a trackball, a track pad, a joystick, wireless remote, a drawing tablet, a voice command system. User input devices 1340 typically allow a user to select objects, icons, text and the like that appear on the monitor 1306 via a command such as a click of a button or the like. User output devices 1330 include all possible types of devices and mechanisms to output information from computer 1302. These may include a display (e.g., monitor 1306), printers, non-visual displays such as audio output devices, etc.

Communications interface 1350 provides an interface to other communication networks, such as communication network 1395, and devices and may serve as an interface to receive data from and transmit data to other systems, WANs and/or the Internet. Embodiments of communications interface 1350 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 1350 may be coupled to a computer network, to a FireWire® bus, or the like. In other embodiments, communications interface 1350 may be physically integrated on the motherboard of computer 1302, and/or may be a software program, or the like.

RAM 1370 and non-volatile storage drive 1380 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 1370 and non-volatile storage drive 1380 may be configured to store the basic programming and data constructs that provide the functionality of various embodiments of the present invention, as described above.

Software instruction sets that provide the functionality of the present invention may be stored in RAM 1370 and non-volatile storage drive 1380. These instruction sets or code may be executed by the processor(s) 1360. RAM 1370 and non-volatile storage drive 1380 may also provide a repository to store data and data structures used in accordance with the present invention. RAM 1370 and non-volatile storage drive 1380 may include a number of memories including a main random access memory (RAM) to store instructions and data during program execution and a read-only memory (ROM) in which fixed instructions are stored. RAM 1370 and non-volatile storage drive 1380 may include a file storage subsystem providing persistent (non-volatile) storage of program and/or data files. RAM 1370 and non-volatile storage drive 1380 may also include removable storage systems, such as removable flash memory.

Bus subsystem 1390 provides a mechanism to allow the various components and subsystems of computer 1302 to communicate with each other as intended. Although bus subsystem 1390 is shown schematically as a single bus, alternative embodiments of the bus subsystem may utilize multiple busses or communication paths within the computer 1302.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known, processes, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

What is claimed is:

1. A smart device, comprising:
   a case;
   a wireless interface that communicates with a remote server system via a wireless network, wherein the wireless interface is located within the case;
   a light sensor that detects an ambient brightness level of an ambient environment of the smart device;
   a motion sensor that detects motion of a user in the ambient environment of the smart device;
   a light that is capable of outputting light into the ambient environment of the smart device; and
   a processing system within the case, the processing system being in communication with the wireless interface, the motion sensor, the light sensor, and the light, the processing system comprising at least one processor and being configured to:
      receive, via the wireless interface, a message indicating that a lighting feature that provides illumination based on movement and the ambient brightness level has been activated;
      receive an indication of the ambient brightness level in the ambient environment of the smart device as sensed by the light sensor;
      determine that the ambient brightness level is less than a threshold brightness value;
      receive information from the motion sensor indicative of the user moving in the ambient environment of the smart device; and
      cause the light to illuminate based on all of the following conditions being present: (1) the message having been received via the wireless interface that indicates that the lighting feature has been activated; (2) the ambient brightness level being below the threshold brightness value; and (3) the user moving in the ambient environment of the smart device.

2. The smart device of claim 1, further comprising a smoke sensor within the case, wherein the smart device is a smoke detector.

3. The smart device of claim 2, wherein the processing system is further configured to disable the lighting feature when an alarm based on smoke being detected by the smoke sensor is active.

4. The smart device of claim 3, wherein the processing system is further configured to cause the light to output light in a different color, animation pattern, or both than the lighting feature when the alarm is active.

5. The smart device of claim 1, further comprising a carbon monoxide sensor within the case, wherein the smart device is a carbon monoxide detector.

6. The smart device of claim 5, wherein the processing system is further configured to disable the lighting feature when an alarm based on carbon monoxide being detected by the carbon monoxide sensor is active.

7. The smart device of claim 6, wherein the processing system is further configured to cause the light to output light in a different color, animation pattern, or both than the lighting feature when the alarm is active.

8. The smart device of claim 1, further comprises a presence detector that captures images.

9. The smart device of claim 1, further comprising a temperature sensor, wherein the smart device is a thermostat.

10. The smart device of claim 1, further comprising a doorbell, wherein the smart device is a smart doorbell.

11. The smart device of claim 1, further comprising: a smoke sensor and a carbon monoxide sensor, wherein the smart device is a smoke detector and carbon monoxide detector.

12. A smart illumination system comprising:
an application executed by a portable electronic device, wherein the application is configured to cause the portable electronic device to:
receive an indication that a lighting feature that provides illumination from a smart device based on movement and an ambient brightness level in an ambient environment of the smart device has been activated; and
transmit a message indicating that the lighting feature has been activated, wherein the smart device is configured to:
receive the message, via a wireless communication module, indicating that the ambient brightness level in the ambient environment of the smart device as sensed by a light sensor, wherein the wireless communication module communicates with a remote server system via a wireless network;
determine that the ambient brightness level is less than a threshold brightness value;
receive information from a motion sensor indicative of a user moving in the ambient environment of the smart device; and
cause a light to illuminate based on all of the following conditions being present: (1) the message having been received via the wireless communication module that indicates that the lighting feature has been activated; (2) the ambient brightness level being below the threshold brightness value; and (3) the user moving in the ambient environment of the smart device.

13. A method for outputting light using a smart device, the method comprising:
receiving, via a wireless interface of the smart device, a message indicating that a lighting feature of the smart device that provides illumination based on movement and an ambient brightness level is to be activated, wherein the wireless interface communicates with a remote server system via a wireless network;
determining, using a light sensor, the ambient brightness level in an ambient environment of the smart device;
determining that the ambient brightness level is less than a threshold brightness value;
detecting, by a motion detector, a user moving in the ambient environment of the smart device; and
illuminating a light of the smart device based on all of the following conditions being present: (1) the message having been received via the wireless interface that indicates that the lighting feature has been activated; (2) the ambient brightness level being below the threshold brightness value; and (3) the user moving in the ambient environment of the smart device.

14. The method of claim 13, further comprising: detecting smoke using a smoke sensor of the smart device, wherein the smart device is a smoke detector.

15. The method of claim 14, further comprising: disabling the lighting feature when an alarm based on smoke being detected by the smoke sensor is active.

16. The method of claim 15, further comprising: illuminating the light of the smart device in a different color, animation pattern, or both than the lighting feature when the alarm is active.

17. The method of claim 13, further comprising: detecting carbon monoxide using a carbon monoxide sensor of the smart device, wherein the smart device is a carbon monoxide detector.

18. The method of claim 17, further comprising: disabling the lighting feature when an alarm based on carbon monoxide being detected by the carbon monoxide sensor is active.

19. The method of claim 13, further comprises capturing one or more presence detector that captures images.

20. The method of claim 13, wherein the smart device is a thermostat or a smart doorbell.

* * * * *